(12) United States Patent
Jeffries et al.

(10) Patent No.: US 8,530,211 B2
(45) Date of Patent: Sep. 10, 2013

(54) CO-FERMENTATION OF GLUCOSE, XYLOSE AND/OR CELLOBIOSE BY YEAST

(75) Inventors: Thomas W. Jeffries, Madison, WI (US);
Laura B. Willis, Madison, WI (US);
Tanya M. Long, Monona, WI (US);
Yi-Kai Su, Madison, WI (US)

(73) Assignees: Wisconsin Alumni Research Foundation, Madison, WI (US); U.S. Department of Agriculture, Washington, DC (US)

( * ) Notice: Subject to any disclaimer, the term of this patent is extended or adjusted under 35 U.S.C. 154(b) by 0 days.

(21) Appl. No.: 13/451,324

(22) Filed: Apr. 19, 2012

(65) Prior Publication Data
US 2012/0270289 A1 Oct. 25, 2012

Related U.S. Application Data

(60) Provisional application No. 61/477,004, filed on Apr. 19, 2011.

(51) Int. Cl.
*C12P 7/06* (2006.01)
*C12P 7/08* (2006.01)
*C12P 7/10* (2006.01)

(52) U.S. Cl.
USPC .......................... 435/161; 435/163; 435/165

(58) Field of Classification Search
None
See application file for complete search history.

(56) References Cited

U.S. PATENT DOCUMENTS
2009/0325241 A1* 12/2009 Jeffries et al. ................. 435/105

OTHER PUBLICATIONS

Nguyen et al., Mycological Research, vol. 110, Issue 10, Oct. 2006, pp. 1232-1241.*

* cited by examiner

*Primary Examiner* — Chris R Tate
*Assistant Examiner* — Douglas F White
(74) *Attorney, Agent, or Firm* — Andrus, Sceales, Starke & Sawall, LLP

(57) ABSTRACT

Provided herein are methods of using yeast cells to produce ethanol by contacting a mixture comprising xylose with a *Spathaspora* yeast cell under conditions suitable to allow the yeast to ferment at least a portion of the xylose to ethanol. The methods allow for efficient ethanol production from hydrolysates derived from lignocellulosic material and sugar mixtures including at least xylose and glucose or xylose, glucose and cellobiose.

20 Claims, 11 Drawing Sheets

CO-FERMENTATION OF GLUCOSE, XYLOSE AND/OR CELLOBIOSE BY YEAST

CROSS-REFERENCE TO RELATED APPLICATIONS

This patent application claims the benefit of priority of U.S. Provisional Patent Application No. 61/477,004, filed Apr. 19, 2011, which is incorporated herein by reference in its entirety.

STATEMENT REGARDING FEDERALLY SPONSORED RESEARCH

This invention was made with government support under DE-FC02-07ER64494 awarded by the US Department of Energy and 10-JV-11111126-053 awarded by the USDA/FS. The government has certain rights in the invention.

FIELD OF THE INVENTION

The invention relates to the field of industrial microbiology and the production of alcohols. More specifically, ethanol is produced from xylose, glucose, cellobiose and mixtures of sugars in acid and enzymatic hydrolysates via industrial fermentation by yeast.

BACKGROUND OF THE INVENTION

Ethanol obtained from the fermentation of starch from grains or sucrose from sugar cane is being blended with gasoline to supplement petroleum supplies. The relatively oxygenated ethanol increases the efficiency of combustion and the octane value of the fuel mixture. Production of ethanol from grain and other foodstuffs, however, can limit the amount of agricultural land available for food and feed production, thereby raising the market prices of grains and leading to the expansion of agricultural production into forests or marginal lands thereby resulting in ecological damage. Moreover, the intense tillage and fertilization of prime agricultural land for the production of grains can result in excessive soil erosion and runoff or penetration of excess phosphorous and nitrogen into waterways and aquifers. Production of ethanol from lignocellulosic agricultural or woody feedstocks that do not compete with food and animal feed supplies is therefore highly desirous, indeed essential for the large-scale development of renewable fuels from biomass.

Several obstacles currently limit the use of biomass for renewable fuel production. The biomass must be pretreated to extract the sugars, lignins and other components from the starting material. Mild conditions for pre-hydrolysis are desirable because they result in the formation of lower amounts of inhibitory components such as furfural, hydroxymethyl furfural and sugar degradation products such as formic acid. The resulting sugars can be present in the form of monosaccharides such as D-glucose, D-xylose, D-mannose, D-galactose and L-arabinose or as various oligomers or polymers of these constituents along with other lignocellulosic components such as acetic acid, 4-O-methylglucuronic acid, and ferulic acid. Glucose in sugar hydrolysates may repress the induction of transcripts for proteins essential for the assimilation of less readily utilized sugars that are also present in hydrolysates, such as xylose, cellobiose, galactose, arabinose, and rhamnose. In addition, the production of ethanol from glucose can attain inhibitory concentrations even before use of other sugars commences. This results in the incomplete utilization of sugars and sugar mixtures in hydrolysates. Glucose in sugar hydrolysates may also repress the induction of transcripts for proteins essential for the depolymerization of cellulose, cellulo-oligosaccharides, xylan, xylo-oligosaccharides, mannan, manno-oligosaccharides, and other more complex hemicelluloses and oligosaccharides derived from them. These poly- and oligo-saccharides can be present in hydrolysates that have been recovered under mild treatment conditions.

Yeasts such as *Saccharomyces cerevisiae* and *Scheffersomyces stipitis* and bacteria such as *Escherichia coli, Zymomonas mobilis* and *Klebsiella oxytoca* have been engineered for the production of ethanol from xylose, arabinose, xylo- and cellulo-oligosaccharides since native strains of these organisms are limited either by low production rates, strong preference for utilization of glucose over xylose, susceptibility to inhibitors, susceptibility to microbial or bacteriophage contamination, high requirements for nutrients, or containment regulations due to the expression of transgenes in order to achieve xylose or cellobiose utilization. There remains a need for yeasts that will ferment glucose, xylose, cellobiose and other sugars from lignocellulosic materials at high rates and yields without these drawbacks.

BRIEF SUMMARY OF THE INVENTION

Methods for fermenting of D-xylose in the presence or absence of D-glucose and optionally cellobiose and to the fermentation of mixtures of D-xylose and D-glucose as they occur in hydrolysates of lignocellulose are provided herein.

The methods include methods of producing ethanol by contacting a mixture comprising xylose with a *Spathaspora* yeast cell under conditions suitable to allow the yeast to ferment at least a portion of the xylose to ethanol. The yeast cell is capable of producing ethanol from xylose or cellobiose wherein at least one cultivation condition increases the fermentation rate or yield from xylose or cellobiose or a mixture of at least one of these sugars. In particular, the xylose or cellobiose may be fermented in the presence of glucose.

In a further aspect, the invention provides methods of generating ethanol, the method comprising culturing the yeast of the invention, as described herein, in a mixture comprising a sugar under conditions such that the yeast converts the sugar to ethanol. In some embodiments, an ethanol yield of at least about 0.30 g ethanol/g sugar consumed is produced. In some embodiments, culture media with ethanol concentrations of at least about 30 g ethanol/l (e.g., at least about 30, 35, 40, 45, 50, 55, 60, 65, 70, 75, 80, 85 g ethanol/l) is produced. In some embodiments, the yeast has an ethanol production rate of at least about 0.5 g/l·h (e.g., at least about 0.5, 0.6, 0.7, 0.8, 0.9, 1.0 g/l·h).

In some embodiments, the sugar converted to ethanol comprises or is cellobiose. In some embodiments, the sugar converted to ethanol comprises or is xylose. In some embodiments, the yeast converts the sugar to ethanol in the presence of glucose.

In another aspect, the invention provides a bioreactor containing an aqueous solution, the solution comprising a yeast and a mixture including xylose, as described herein. In some embodiments, the volume of the solution is at least 100, 500, 1000, 10,000, 100,000 or 1,000,000 liters.

With respect to the compositions and methods, in some embodiments, the yeast is of the genus *Spathaspora*, in particular the yeast is a *Spathaspora passalidarum*. In some embodiments, the yeast is *Spathaspora passalidarum* NN245, deposited with the Agricultural Research Service as Deposit Number NRRL Y-50740. In some embodiments, the yeast is *Spathaspora passalidarum* NRRL Y-27907 or derivatives thereof. In some embodiments, the yeast are novel isolates of *Spathaspora passalidarum* as determined by D1/D2 sequence similarities in the ITS1 and the ITS2 regions falling within the range considered as belonging to a single yeast species.

The various embodiments of the invention can be more fully understood from the following detailed description, the figures and the accompanying descriptions, which form a part of this application.

BRIEF DESCRIPTION OF THE DRAWINGS

FIG. 4B is a graph showing the specific xylose utilization rate as a function of glucose concentration (B).

DETAILED DESCRIPTION

Figure 1:
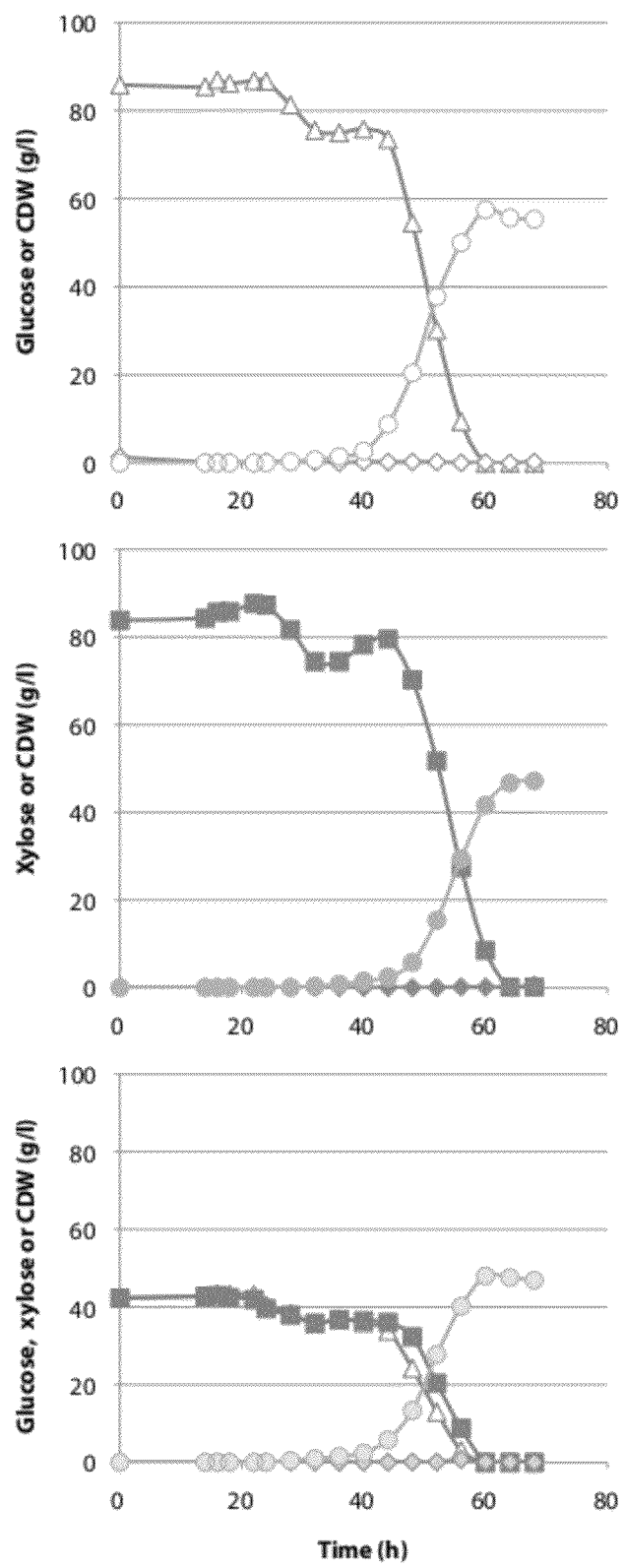
FIG. 1 is a set of graphs showing the growth of *Spathaspora passalidarum* in defined minimal medium with glucose (A), xylose (B) or a mixture of glucose and xylose (C) as the carbon sources under fully aerobic conditions. Cells were cultivated at 30° C. in 2000 ml and were aerated with 1 vvm air and an agitation rate of 700 rpm. Symbols: glucose, open triangles; xylose, solid squares; cell mass, circles; ethanol, diamonds.

Methods of fermentation of D-xylose in the presence or absence of D-glucose and optionally cellobiose and to the fermentation of mixtures of D-xylose, D-glucose and cellobiose as they occur in hydrolysates of lignocellulose are provided herein. The methods include production of ethanol by contacting a mixture comprising xylose with a *Spathaspora* yeast cell under conditions suitable to allow the yeast to ferment at least a portion of the xylose to ethanol. The yeast cell is capable of producing ethanol from xylose or cellobiose wherein at least one cultivation condition increases the fermentation rate or yield from xylose or cellobiose or a mixture of at least one of these sugars as compared to fermentation by yeast such as *Saccharomyces cerevisiae*. In particular, the xylose or cellobiose may be fermented in the presence of glucose.

The mixture comprising xylose is suitably derived from biomass or a lignocellulosic material. Lignocellulosic materials from agricultural residues, fast-growing hardwoods and processing byproducts constitute a large domestic renewable resource that could be used in a sustainable manner for the production of renewable fuels such as by the methods described herein. Substrates presently available in or adjacent to existing grain and sucrose fermentation facilities include grain hulls, corn cobs, corn stalks (stover), sugarcane bagasse, wheat straws various annual or perennial grasses such as *Miscanthus* species, *Sorghum* species, giant reed (*Arundo donax*), and switchgrass (*Panicum virgatum*). Other applicable feedstocks include residues from wood harvest or thinning operations, fast-growing hardwoods such as species of *Populus, Sailix* and *Acer*, and other fast-growing or invasive species. Those of skill in the art will appreciate that other xylose containing materials could be utilized in the methods described herein.

Sugars, lignin and various other components can be extracted from these feedstocks following appropriate mechanical, chemical, thermal or other pretreatments to form the mixtures comprising xylose used in the methods described herein. These include the use of heat, steam, dilute and concentrated acids or bases, and organic solvents either alone, sequentially to or in combination with mechanical maceration. The pretreatment processes result in the formation of soluble hemicellulosic sugars and oligomeric materials along with partially degraded cellulose, hemicellulose and lignin. Ideally, pretreatments minimize substrate losses and byproduct toxin formation while maximizing the production of sugars available for fermentation.

Sugars can be present in the form of monosaccharides such as D-glucose, D-xylose, D-mannose, D-galactose and L-arabinose or as various oligomers or polymers of these constituents along with other lignocellulosic components such as acetic acid, 4-O-methylglucuronic acid, and ferulic acid. From angiosperms the prevalent sugar polymers are cellulose and xylan, which can be hydrolyzed to glucose and xylose, respectively. Glucose is often present in hydrolysates along with xylose and other sugars. Thus as described herein, a yeast capable of fermenting xylose in the presence of glucose is useful.

Glucose in sugar hydrolysates represses the induction of transcripts for proteins essential for the assimilation of less readily utilized sugars that are also present in hydrolysates in other methods. The latter include xylose, cellobiose, galactose, arabinose, and rhamnose. In such cases, the less readily utilized sugars can be referred to as "glucose repressible carbon sources". Glucose in sugar hydrolysates also often represses the induction of transcripts for proteins essential for the depolymerization of cellulose, cellulo-oligosaccharides, xylan, xylo-oligosaccharides, mannan, manno-oligosaccharides, and other more complex hemicelluloses and oligosaccharides derived from them. These poly- and oligo-saccharides can be present in hydrolysates that have been recovered under mild treatment conditions. Mild conditions for pre-hydrolysis are desirable because they result in the formation of lower amounts of furfural, hydroxymethyl furfural and sugar degradation products such as formic acid. Also, extraction of hemicellulose as oligosaccharides facilitates their recovery and separation by ultrafiltration and reverse osmosis from contaminants such as acetic acid. Oligosaccharides and partially hydrolyzed polysaccharides are abundant in the residual solids of lignocellulosic materials that have been subjected to mild pre-hydrolysis. Repression of the enzymes responsible for hydrolysis of poly- and oligo-saccharides can prevent, restrict or inhibit the partial or complete consumption of these substrates. It is therefore highly desirable to obtain microbes that can metabolize or co-metabolize these substrates by producing polysaccharide and oligosaccharide depolymerases in the presence of glucose.

Non-carbohydrate components of hydrolysates such as acetic, ferulic, and 4-O-methylglucuronic acids, furfural, hydroxymethyl furfural, and various degradation products of lignin can be more inhibitory to the metabolism of glucose repressible carbon sources than they are to the metabolism of glucose. If glucose represses the consumption or metabolism of these inhibitors, the initial presence of glucose will enable the further inhibition of glucose repressible carbon sources. It is therefore highly desirable to identify strains or conditions in which the presence of glucose enables the co-utilization of inhibitory non-carbohydrate constituents.

Genes coding for metabolism of xylose, arabinose, mannose, rhamnose, other carbohydrates such as cellobiose, xylan, or cellulose, hemicellulose or other oligo- and polysaccharides can be present in the genome but not expressed at sufficient levels for optimal substrate uptake or product formation. This is especially true of fermentation processes that require a high glycolytic flux. By altering the expression of genes critical for substrate uptake or product formation, it is possible to obtain significantly higher rates of fermentation.

Expression array technology to measure the levels of mRNA in cells (transcriptomics) and assays of intracellular and extracellular metabolites (metabolomics) can provide insights into rate-limiting metabolic steps. By assaying the levels of mRNA transcripts in cells cultivated on different carbon sources or different aeration conditions, it is possible to determine which transcripts are induced or repressed under each condition. For example by cultivating cells in medium containing xylose with or without glucose, it is possible to estimate which transcripts are formed when only xylose is present and which are formed when glucose is present along with xylose. Likewise, assays of transcripts following cultivation under high or low aeration levels can indicate which transcripts are induced. This approach is particularly useful when the cultivation conditions and physiological responses such as ethanol production are correlated with transcript formation. Expression can be altered through molecular biological techniques such as by altering the promoter, increasing the gene copy number, or increasing transcript stability or by changing the environmental conditions in order to induce higher levels of critical enzymes.

Many yeasts and other fungi will assimilate xylose under aerobic conditions, but a relatively small number have been reported to ferment it to ethanol. These include *Pachysolen tannophilus, Candida shehatae, Scheffersomyces (Pichia) stipitis, Pichia segobiensis, Candida tenuis, Candida lyxosophila, Candida jeffriesii, Spathaspora passalidarum*, and *Spathaspora arborariae*. Some yeasts such as *Candida guilliermondii, Candida maltosa*, and *Candida boidinii* will produce small amounts of ethanol from xylose but mainly produce xylitol. Of the yeasts producing ethanol, *S. stipitis* has been the best studied. It was the first native xylose fermenting yeast for which a transformation system was developed, and it was the first native xylose fermenting yeast for which a full genome sequence was obtained.

The physiological capacities of yeasts with respect to ethanol production from xylose vary widely and not necessarily in a manner directly dependent on their taxonomic relationships. For example, *Candida materiae* does not produce ethanol from xylose even though it is closely related to *C. jeffriesii, C. lyxosophila, S. passalidarum* and *S. arborariae*, all of which mainly produce ethanol from xylose. The closely related yeasts *S. stipitis, P. segobiensis*, and *C. shehatae* all will ferment xylose to ethanol but they, along with the *Spathaspora* cluster are taxonomically distant from *C. tenuis*, which is also a species that produces ethanol from xylose. *C. maltosa, C. guilliermondii*, and *C. boidinii*, all of which produce some ethanol but larger amounts of xylitol from xylose are not closely related to one another or to the yeast species that predominantly produce ethanol.

The yeast *Spathaspora passalidarum* was first described by Nguyen, Marshall and Blackwell in 2006 and is referenced as strain NN245 (9). In this paper, morphological and physiological observations were performed "according to established methods" (35, 36). The fermentation of xylose is reported as "+" without further elaboration as to quantity or rate of production. A deposit of the culture (NRRL Y-27907) was made to the NRRL Yeast collection at National Center for Agricultural Utilization Research in Peoria, Ill., USA. NN245 was also deposited with the Agricultural Research Service as Deposit Number NRRL Y-50740 under the terms of the Budapest Treaty on Apr. 13, 2012.

A yeast strain belonging to the species *Spathaspora arborariae* was reported to produce ethanol from xylose, glucose or a mixture of xylose and glucose when cells pre-grown on rich medium are harvested, concentrated and incubated with solutions of the pure sugars in rich medium. Cells (11.3 g/l) of *S. arborariae* pre-grown on 1% yeast extract, 1% peptone (YP) and 2% glucose have been reported to ferment a solution of YP plus 20 g/l glucose to produce 9.13 g/l ethanol in 2 h for a specific fermentation rate of 0.404 g/g dry wt cells·h. Cells (13 g dry wt/l) of *S. arborariae* pre-grown on YP and 2% xylose have been reported to ferment a solution of YP plus 19.1 g/l xylose to produce 8.9 g/l ethanol in 4 hours for a specific fermentation rate of 0.17 g ethanol/g dry wt cells h. A pre-grown cell suspension (13.4 g dry wt/l) of *S. arborariae* has been reported to consume glucose at a rate of 0.59 g/g cells·h and xylose at a rate of 0.07 to 0.08 g/g dry wt cells·h when ca. 20 g/l of glucose and 20 g/l of xylose were both present in the medium (10). This report did not specify the cultivation of yeasts belonging to the genus *Spathaspora* in a defined minimal medium or in medium containing or predominantly consisting of hydrolysate derived from lignocellulose. This report further did not specify adaptation of such yeasts to growth in hydrolysate. Further, this report did not demonstrate or specify the capacity for simultaneous utilization of a mixture of glucose and xylose under fully aerobic conditions nor the more rapid utilization of xylose than glucose under oxygen limiting conditions.

Methods of producing ethanol from a xylose containing material or a mixture comprising xylose by fermenting the mixture or material with a *Spathaspora* yeast cell. Suitably the *Spathaspora* yeast cell is *Spathaspora passalidarum*, suitably *Spathaspora passalidarum* NN245. In some embodiments, the yeast are novel isolates of *Spathaspora passalidarum* as determined by D1/D2 sequence similarities in the ITS1 and the ITS2 regions falling within the range considered as belonging to a single yeast species. A single yeast species may vary by about 1% in these sequences. See Sugita and Nishikawa, J Health Science 49:531-533 (2003) and Nagahama et al., Intl J Systematic and Evolutionary Microbiol 56: 295-299 (2006) both of which are incorporated herein by reference in their entireties. By "xylose-containing material" or "mixture containing xylose" it is meant any medium comprising xylose or glycosidic polymers of xylose, whether liquid or solid. Suitable xylose-containing materials include, but are not limited to, hydrolysates of polysaccharide or lignocellulosic biomass such as corn hulls, wood, paper, agricultural by-products, and the like.

The xylose may be present at any level within the mixture. Suitably the xylose is present in the mixture at least at 5 g/l, 10 g/l, 15 g/l, 20 g/l, 25 g/l, 30 g/l, 35 g/l, 40 g/l, 45 g/l, 50 g/l, 55 g/l, 60 g/l, 65 g/l, 70 g/l, 75 g/l, 80 g/l, 85 g/l, 90 g/l, 95 g/l, 100 g/l, 110 g/l, 120 g/l, 130 g/l or even more. The xylose containing material or the mixture comprising xylose may also comprise other components derived from a biomass or lignocellulosic material such as glucose, cellobiose, arabinose and rhamnose.

Suitably, the mixture further comprises glucose. Suitably the mixture comprises less than or equal to about 120 g/l, 110 g/l, 100 g/l, 90 g/l, 80 g/l, 70 g/l, 60 g/l, 50 g/l, 40 g/l, 35 g/l, 30 g/l, 25 g/l, 20 g/l, 15 g/l, 10 g/l, 5 g/l or even less glucose. Suitably, the yeast is capable of fermenting the glucose and xylose to produce ethanol under the conditions utilized. Suitably the ratio of xylose to glucose in the mixture is between about 5:1 and 2:3 by weight. Suitably the ratio of xylose to glucose is about 5:3 by weight. Suitably the mixture further comprises cellobiose. Suitably the mixture further comprises at least about 1 g/l, 2 g/l, 3 g/l, 4 g/l, 5 g/l, 10 g/l, 15 g/l, 20 g/l, 25 g/l, 30 g/l, 35 g/l, 40 g/l, 45 g/l, 50 g/l, 55 g/l, 60 g/l, 65 g/l, 70 g/l or more cellobiose. Suitably the yeast is capable of fermenting the cellobiose and xylose to produce ethanol under the conditions utilized. Suitably, the mixture may comprise at least xylose, glucose and cellobiose and the yeast is capable of fermenting all three and producing ethanol from at least a portion of all three carbon sources under the conditions utilized.

*Spathaspora* yeast have minimal growth requirements and grow on and ferment the above-noted sugars well in a minimal medium such as those described in the Examples. The yeast cells require about 0.2 to about 2 g/l of a nitrogen source in the medium. Suitably the nitrogen is about 1 g/l in the mixture. Sources of nitrogen include but are not limited to urea, corn steep liquor, or lysamine. Those of skill in the art will appreciate that other sources of nitrogen may be used in the mixture.

The conditions utilized may include oxygen limitation. Those of skill in the art will appreciate that the aeration requirements of the methods are important to establishing fermentation of the sugars in the mixture to ethanol. Suitably the oxygen is limited during fermentation and the oxygen in the mixture is less than 2.1%. Suitably the oxygen levels in the culture medium are less than 2%, 1%, 0.5% or even lower. Suitably the methods are carried out in a bioreactor. The bioreactor may be a 1 L, 2 L, 4 L, 10 L, 100 L, 500 L, 1,000 L, 5,000 L, 10,000 L, 50,000 L, 100,000 L or even a 1,000,000 L bioreactor. The temperature maintained during the method may be between 20° C. and 45° C., suitably between 25° C. and 35° C., suitably about 30° C. Suitably the mixture is agitated during the method, the agitation can be varied throughout the method to obtain optimal results or it may be kept at a standard level. Suitably the agitation is between 50 rpm and 700 rpm, suitably between 100 rpm and 500 rpm, suitably between 150 rpm and 300 rpm. Those of skill in the art will appreciate that the oxygen levels in the sparging gases and the agitation rates may be optimized to achieve the best fermentation results. The oxygen transfer rate is suitably between 1.0 and 4.5 mmol $O_2$/l·h, more suitably between about 1.25 and 3.5 mmol $O_2$/l·h, more suitably between 1.5 and 2.5 mmol $O_2$/l·h.

By a "hydrolysate" as used herein, it is meant a polysaccharide that has been depolymerized through the addition of water to form mono and oligosaccharides. Hydrolysates may be produced by enzymatic or acid hydrolysis of the polysaccharide-containing material, by a combination of enzymatic and acid hydrolysis, or by another suitable means. The hydrolysate may be from corn stover, grain hulls, corn cobs, sugarcane bagasse, wood chips, wood pulp, softwood, hardwood, pine, loblolly pine, maple, switchgrass (*Pancium virgatum*), *Miscanthus*, date palm (*Phoenix dectylifera*), oil palm, *Sorghum*, *Arundo donax* or other biomass derived materials. Suitably the hydrolysate is an acid or enzymatic hydrolysate. The polysaccharide hydrolysate may be in aqueous solution, concentrated or dehydrated. The hydrolysate may be obtained following treatment with calcium or magnesium hydroxide, ammonia, sulfuric, sulfurous, oxalic or phosphoric acid, precipitation, centrifugation, extraction with organic solvents or ionic liquids or it may be obtained following filtration, ultrafiltration, dialysis, pervaporation, electrodialysis or reverse osmosis.

In some embodiments, *Spathaspora* yeast adapted for growth in the hydrolysate or in components found in the hydrolysate may be used in the methods. Yeast may be adapted for growth in the hydrolysates by methods known to those of skill in the art, including via genetically engineering *Spathaspora* yeast adapted for growth in the hydrolysates and serial passage in increasing concentrations of the hydrolysate or components found in the hydrolysates to select for yeast capable of tolerating or thriving in higher concentrations of hydrolysates or of ethanol or acids. As shown in the Examples, mixtures of yeast cells were serially passaged in hydrolysate to select for yeast strains better able to ferment the hydrolysate. Notably the yeast may be adapted in one type of hydrolysate and may be found to ferment a distinct hydrolysate better than the parent strain from which it was adapted. In particular, the yeast were able to produce additional ethanol during the fermentation and were able to withstand higher concentrations of acetic acid, such as 5.0 g/l, 4.0 g/l, 3.5 g/l, 3.0 g/l, 2.5 g/l, 2.0 g/l, 1.8 g/l, 1.6 g/l, 1.4 g/l, 1.2 g/l or 1.0 g/l.

In some embodiments, the hydrolysate is subjected to saccharification either before or simultaneous with the method described herein for producing ethanol.

The methods of generating ethanol from a mixture comprising xylose under conditions such that the yeast converts the sugar to ethanol may provide an ethanol yield of at least about 0.30 g ethanol/g sugar consumed. In some embodiments, ethanol concentrations of at least about 30 g ethanol/l (e.g., at least about 30, 35, 40, 45, 50, 55, 60, 65, 70, 75, 80, 85 g ethanol/l) is produced. In some embodiments, the yeast has an ethanol production rate of at least about 0.5 g/l·h (e.g., at least about 0.5, 0.6, 0.7, 0.8, 0.9, 1.0 g/l·h) over the duration of the fermentation. In some embodiments the ethanol production rate may be as high as 1.5 g/l·h (e.g., as high as 1.5, 1.4, 1.3, 1.2, 1.1, or 1.0 g/l·h). Suitably, the ethanol production rate is between these ranges.

It is understood that the examples and embodiments described herein are for illustrative purposes only and that various modifications or changes in light thereof will be suggested to persons skilled in the art and are to be included within the spirit and purview of this application and scope of the appended claims. All publications, sequences or GenBank Accession numbers, patents, and patent applications cited herein are hereby incorporated by reference in their entirety for all purposes.

EXAMPLES

The following examples are offered to illustrate, but not to limit the claimed invention.

Example 1

Aerobic Cultivation

A culture of *Spathaspora passalidarum* NN245 (9) was isolated by Prof. Meredith Blackwell and collaborators at the Department of Biological Sciences, Louisiana State University, Baton Rouge, La. 70803, USA. A deposit of the culture (NRRL Y-27907) was made to the NRRL Yeast collection at National Center for Agricultural Utilization Research in Peoria, Ill., USA. NN245 was also deposited with the Agricultural Research Service as Deposit Number NRRL Y-50740 under the terms of the Budapest Treaty on Apr. 13, 2012. These cultures are considered synonymous and equivalent in all examples reported herein. Cells were routinely sub-cultured in Petri dishes containing Yeast extract (1%), Peptone (1%) and either Glucose (2%) or Xylose (2%) (YPG or YPX, respectively) plus 18 to 20 g/l agar. For long-term storage, cells were suspended in 0.5 ml of distilled water; an equal volume of sterile 30% glycerol was added; the cell suspension was dispensed to sterile vials and frozen at −80° C. Cells were recovered from the frozen state by streaking onto a YPG plate.

Inocula were cultivated in 50 ml of YP medium (g l$^{-1}$): yeast extract, 20; peptone, 10 plus 60 g·l$^{-1}$ glucose or xylose in 125 ml Erlenmyer flasks at 30° C. under high aeration (200 rpm). After 24 h, cells in 50 ml of medium were centrifuged, washed once in sterile distilled water, suspended in an appropriate volume of sterile water, and used as inoculum for the bioreactors. Following inoculation the cell suspension had an optical density at 600 nm (OD$_{600}$) of 0.05, which was equivalent to 0.0075 mg/ml dry wt of cells.

The defined minimal medium (CBS) formulation for bioreactor cultivation was modified from Verduyn (37). It contained nitrogen, trace metal elements and vitamins in the following amounts (g l$^{-1}$): urea, 2.4; KH$_2$PO$_4$, 3; MgSO$_4$.7H$_2$O, 0.5; (ml l$^{-1}$): trace element solution, 1; vitamin solution, 1; and antifoam 289 (Sigma A-8436), 0.05. Carbon sources consisted of 80 g/l D-glucose, D-xylose, or a 50/50 mixture of 40 g/l glucose and 40 g/l xylose. The carbon sources were dissolved in distilled water, taken up to 97.5% of the working volume (i.e. 1.95 L) and steam sterilized in the reactor vessels along with dissolved oxygen and pH probes at 121 psig for 45 min. After the vessels and medium cooled, 50 ml of a sterile 40-fold concentrate of the basal medium was added the reactor vessel.

Cultivation was performed in New Brunswick Scientific Bio Flo 110 3-L bioreactors with working volumes of 2 L each. Each bioreactor was equipped with two sets of flat blade impellers and gassed from the bottom through a circular sparging ring.

For Example 1, the bioreactor temperature was controlled at 30° C. and pH was kept constant at 5.0±0.1 by automatic addition of 5 N KOH. Airflow for aerobic cultivations was 1 vvm and the agitation rate was 750 rpm. This aeration rate is operably defined as "fully aerobic conditions".

Under fully aerobic conditions *S. passalidarum* NN245 exhibited a long lag phase (≈22 h) in which no significant growth could be determined by a measurement of the optical density (FIG. 1). Between 32 and 40 h in the case of glucose and between 36 and 44 h in the case of xylose, the time required for the cell mass to double was 9.4 h in the case of glucose and 9.1 h in the case of xylose. The growth rate increased over the following 4 to 8 h reaching a minimum doubling time of 2.8 h in the case of glucose and 3.5 h in the case of xylose. After 56 or 60 h, the glucose or xylose was exhausted and the accumulation of cell mass ceased. Even though the cell growth rate was higher with glucose than with xylose, the specific xylose uptake rate was higher with xylose (0.53 g substrate/g cells h$^{-1}$) than with glucose (0.26 g substrate/g cells h$^{-1}$), and the cell yield was lower for xylose (0.54 g cells/g xylose consumed) than for glucose (0.67 g cells/g xylose consumed). For a mixture of glucose and xylose, the initial doubling time was very long (≈30 h) before decreasing to a minimum of ≈3.7 h. No ethanol production was observed under fully aerobic conditions.

TABLE 1

Growth and substrate kinetic calculations based on cultivation of S. spathaspora on minimal defined medium under fully aerobic conditions.

|  | Time to double (h) | Specific substrate uptake rate (g/g · h) | Yield (g/g consumed) |
|---|---|---|---|
| Glucose (86 g/l) | 9.41 | 0.26 | 0.67 |
| Xylose (86 g/l) | 9.08 | 0.53 | 0.54 |
| Glucose:xylose (43:42 g/l) | 30 | 0.33 | 0.56 |

This example illustrates that under fully aerobic conditions, the growth rates of S. passalidarum on glucose or xylose are similar, that the specific substrate uptake rate with xylose is greater than with glucose and that the cell yield is lower with xylose than with glucose. The results further illustrate that under fully aerobic conditions, glucose and xylose are consumed concurrently. Under fully aerobic conditions, therefore, glucose does not repress xylose utilization.

Example 2

Aerobic Cultivation Followed by Oxygen-Limited Growth and Ethanol Production

Cells of Spathaspora passalidarum NN245 were transferred from a 24-48 h-old plate of YPG into 50 ml of YP medium with 2% D-xylose or D-glucose in 125 ml Erlenmeyer flasks at 30° C. under high aeration (200 rpm) and incubated for 18 to 24 h. Cells were then centrifuged, washed once in sterile distilled water and used to inoculate duplicate bioreactors containing CBS with either glucose or xylose as the carbon source for each set of reactors. Cells from YPX were used to inoculate CBS medium with xylose, YPG were used to inoculate CBS with xylose. The starting cell density in the bioreactor for Example 2 was 0.11 g cell dry wt (cdw) per liter.

For Example 2, the bioreactor temperature was controlled at 25° C. and pH was kept constant at 5.0±0.1 by automatic addition of 5 N KOH. Airflow for aerobic cultivations was 0.5 vvm and the agitation rate was 500 rpm. From 0 h until 12.5 h cultures were flushed with air. Samples were removed for sugar, ethanol and cell dry wt analyses at 0, 3, 8.5 and 12.5 h. The dissolved oxygen (DO) monitor showed DO levels between 70% and 30% of air saturation during this time. No significant ethanol production was detected. At 12.5 h, samples were removed for transcriptomics and metabolomics analysis, and the sparging gas (air) was diluted with 90% nitrogen without altering the volumetric flow rate or the agitation rate. This condition is operably defined as "oxygen limitation". The DO quickly dropped to a value below the sensitivity of the probe (<0.2% air saturation) and ethanol production started shortly after oxygen limitation.

Figure 2:
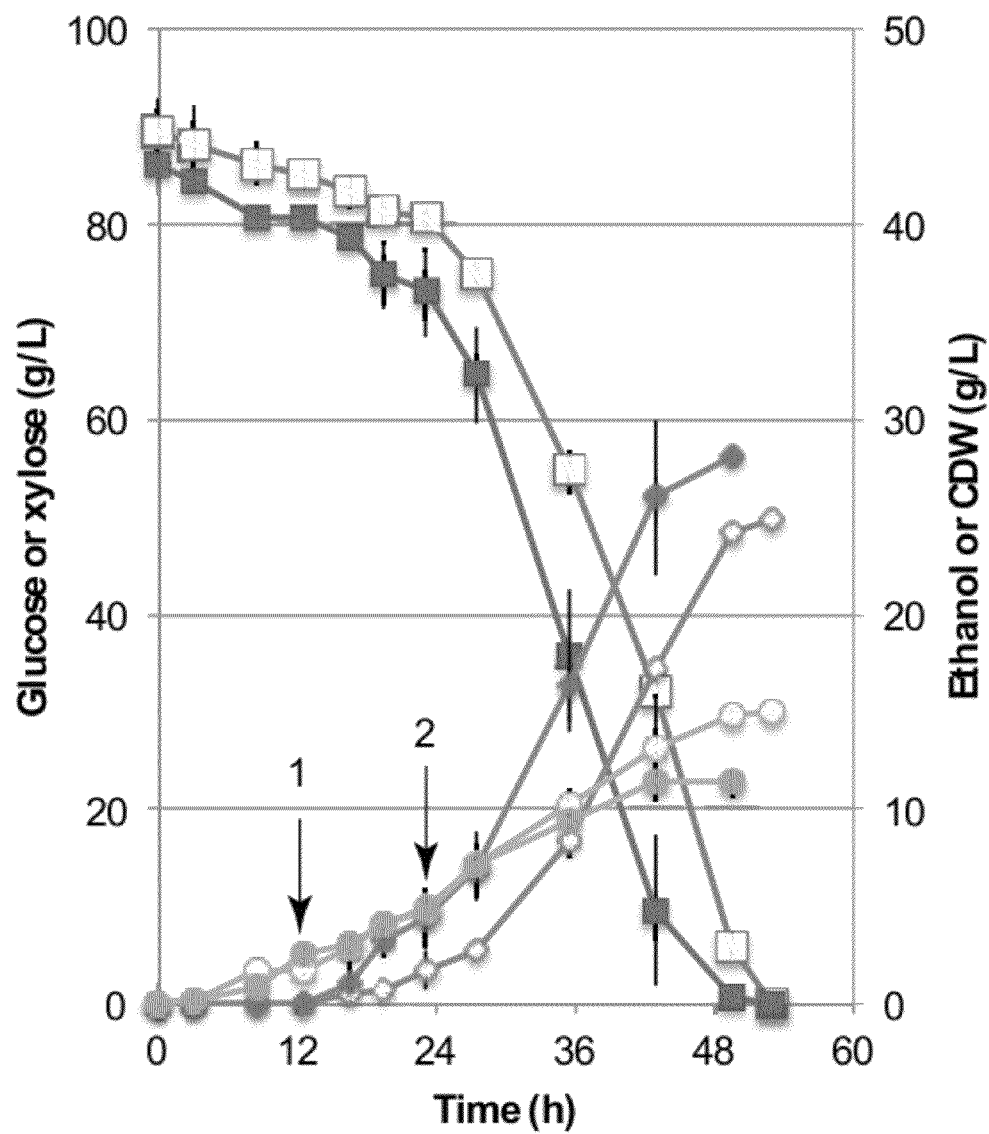
FIG. 2 is a graph showing growth of and ethanol production by *Spathaspora passalidarum* in minimal medium with glucose or xylose as the carbon source under oxygen limiting conditions following an aerobic growth phase. Cells were cultivated in defined minimal medium under aerobic conditions for the first 12.5 h. Subsequently they were cultivated under oxygen limiting conditions. Arrow (1) shows the point at which cultures were switched from 21% oxygen (air) to 2.1% oxygen (air plus 90% nitrogen) and the first transcriptomics samplings. Arrow (2) shows the point for the second transcriptomics and metabolomics samplings. Averages of results from two bioreactors are shown. Error bars indicate the standard deviation. Solid symbols, xylose; open symbols, glucose; squares, sugar; circles, cell mass; diamonds, ethanol.

As can be observed from FIG. 2, the carbon source was depleted first in the bioreactors containing xylose and subsequently in the bioreactors containing glucose. Ethanol production rates were higher in the xylose-containing bioreactors than in the glucose-containing bioreactors. The overall cell yields in the xylose-containing bioreactors were lower. The combination of higher ethanol accumulation and lower cell accumulation resulted in higher ethanol yields for ethanol from xylose than from glucose (Table 2).

TABLE 2

Fermentation kinetics derived from Example 2.

|  | Glucose | Xylose |
|---|---|---|
| Substrate uptake rate (g/g cdw · h) | 0.25 | 0.36 |
| Ethanol production rate (g/g cdw · h) | 0.07 | 0.12 |
| Cell yield (g cdw/g substrate) | 0.165 | 0.132 |
| Ethanol yield (g ethanol/g substrate | 0.278 | 0.326 |

The results from Example 2 show that under oxygen limitation Spathaspora passalidarum will take up xylose faster than glucose and produce ethanol at a higher rate from xylose than from glucose. The cell yield is lower and the ethanol yield is higher with xylose than with glucose.

Example 3

Oxygen Limited Growth and Fermentation

Cells of Spathaspora passalidarum NN245 were transferred from a 24-48 h-old plate of YPG into 50 ml of YP medium with 6% D-xylose or D-glucose in 125 ml Erlenmeyer flasks at 30° C. under high aeration (200 rpm) and incubated for 18 to 24 h to create "seed inocula". The cells from the seed inocula were transferred without washing to 200 ml of YP medium with 6% D-xylose or D-glucose in 1-L Erlenmeyer flasks at 30° C. under high aeration (200 rpm) and incubated for 24 h. Cells were transferred directly from the final seed flask into the bioreactor without washing. Cell densities were measured and equivalent amounts of cells were used to inoculate each bioreactor. One flask of seed inoculum (≈250 ml) was used to inoculate one bioreactor. This method of cell cultivation enabled growth and ethanol production under oxygen limited conditions such that the cells were fermenting at the time they were sub-cultured into the bioreactors.

The dissolved oxygen (DO) levels in the bioreactors were calibrated to 10% of air saturation at 25° C. prior to inoculation by sparging the vessels with a mixture of 90% $N_2$ and 10% air (2.1% oxygen). The sparging gas was then set to 100% air, and the DO controller was set to maintain the previously calibrated 10% DO by cascading the rpm, not exceeding a maximum rpm of 300 or a minimum of 50 rpm while $OD_{600}$ was below 20 to 25. When the $OD_{600}$ was above 20 to 25, the sparging gas was 10% air and 90% nitrogen (2.1% $O_2$), and the agitation rate was set at 500 rpm. The bioreactors were inoculated with 250 ml of cell culture fluid per 2000 ml of initial bioreactor volume. After the inocula were added to the bioreactors, the initial mixing rate was 50 rpm due to the low oxygen uptake rate of the cells. The starting cell density in the bioreactor was ≈1.23 g/l ($OD_{600}$≈7.3). After the cells and broth were added to the bioreactors, the initial mixing rate was 50 rpm. Gradually, as the cell population increased in number and respiration capacity, the DO controller increased the agitation rate to keep the air saturation at 10% (2.1% oxygen) while sparging with air (21% oxygen), eventually the rpm reached the preset maximum of 300. As the cell concentration continued to increase due to growth, the DO level began to fall. After 7 h of growth, when the cell density had attained an $OD_{600}$ of 22.7 for glucose and 23.1 for xylose (≈4.45 and ≈3.15 g/l, respectively), the sparging gas was switched to a mixture of 90% $N_2$ and 10% air (≈0.21% $O_2$) and the agitation rate was increased to 500 rpm. Immediately after this switch, the DO fell below the detectable limit of the DO probe and ethanol began to accumulate in the bioreactor.

Figure 3:
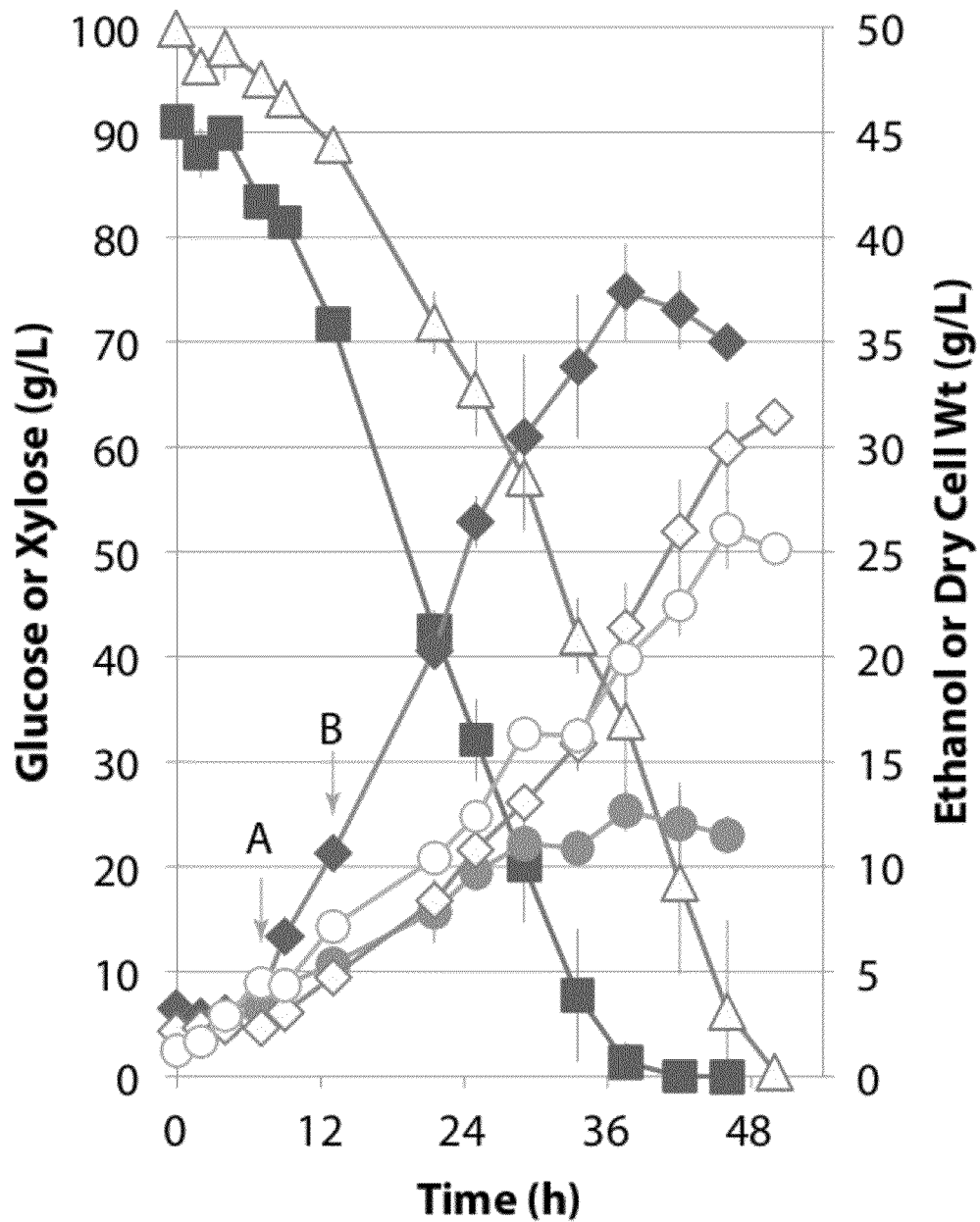
FIG. 3 is a graph showing the growth of and ethanol production by *Spathaspora passalidarum* in minimal medium with glucose or xylose as the carbon source under oxygen limiting conditions following an oxygen limited growth phase. Cells were cultivated in defined minimal medium while sparged with air and while keeping the DO level to 10% air saturation (≈2% oxygen saturation) by limiting the RPM for the first 7 h. Subsequently cells were cultivated under oxygen limiting conditions (2% oxygen) by switching the sparging gas from air to a mixture of 90% $N_2$ and 10% air. Arrow (A) shows the point at which cultures were switched from 21% oxygen (air) to 2.1% oxygen (air plus 90% nitrogen) and the first transcriptomics samplings. Arrow (B) shows the point for the second transcriptomics and metabolomics samplings. Averages of results from two bioreactors are shown. Error bars indicate the standard deviation. Solid symbols, xylose; open symbols, glucose; squares, sugar; circles, cell mass; diamonds, ethanol.

As can be seen in FIG. 3, a small amount of ethanol was present at the start of the bioreactor cultivation. This was attributable to ethanol that accumulated in the medium during production of the seed inoculum. Cell densities increased linearly following inoculation but ethanol did not accumulate further until the sparging gas was switched to 90% $N_2$ and 10% air. Xylose was depleted more rapidly than glucose and more ethanol accumulated in the bioreactors containing xylose than in the bioreactors containing glucose. Surprisingly, the cell yield was significantly lower on xylose than on glucose.

The specific ethanol production rate was highest immediately following the transition from air to 10% air and declined steadily after that time until all of the substrate was consumed. Initially the specific xylose utilization rate (g ethanol/g dry wt cells·h) was about 4.6 times higher with xylose than with glucose. This declined gradually over the following 24 h until the specific fermentation rate was about 1.7 times higher with xylose than with glucose (Table 3). By comparison, the average cell yields from glucose or xylose during this period were 0.26 g cdw/g glucose and 0.2 g cdw/g xylose, respectively.

From the results of Example 3, we can conclude that a high initial cell density and a gradual transition to oxygen limitation initiate a high rate of xylose conversion to ethanol. Under these conditions, the specific rate of ethanol production is lower and the cell growth rate and yield are higher on glucose than on xylose. Both ethanol production and cell growth are approximated by linear functions of the aeration rate, which was constant, but as cell densities increase, the specific ethanol production rate decreases.

TABLE 3

Specific fermentation rates of cells cultivated on glucose or xylose following a switch from air to 10% air at 7 h.

| Time (h) | g EtOH/g cdw·h glucose | g EtOH/g cdw·h xylose | Ratio of specific fermentation rates (xylose/glucose) |
|---|---|---|---|
| 9.00 | 0.085 | 0.389 | 4.6 |
| 13.00 | 0.075 | 0.202 | 2.7 |
| 21.50 | 0.048 | 0.172 | 3.6 |
| 25.00 | 0.062 | 0.199 | 3.2 |
| 29.00 | 0.039 | 0.097 | 2.5 |
| 33.50 | 0.038 | 0.065 | 1.7 |

Example 4

Fermentation of a Mixture of Glucose and Xylose

Cells of *Spathaspora passalidarum* NN245 were transferred from a 24-48 h-old plate of YPG into 50 ml of YP medium with 3% D-xylose and 3% D-glucose in 125 ml Erlenmeyer flasks at 30° C. under high aeration (200 rpm) and incubated for 18 to 24 h to create "seed inocula". The cells from the seed inocula were transferred without washing to 200 ml of YP medium with 3% D-xylose and 3% D-glucose in 1-liter Erlenmeyer flasks at 30° C. under high aeration (200 rpm) and incubated for 24 h. Cells were transferred directly from the final seed flask into the bioreactor without washing. Cell densities were measured and equivalent amounts of cells were used to inoculate each bioreactor. About 250 ml of seed inoculum was used to inoculate one bioreactor to a final volume of 2 l. This method of cell cultivation enabled growth and ethanol production under oxygen limited conditions such that the cells were fermenting at the time they were subcultured into the bioreactors. The bioreactors contained CBS medium with 50 g/l glucose plus 50 g/l xylose. The initial cell densities ($OD_{600}$) of the bioreactors were ≈8.5 (≈1.26 g cdw/l).

The sparging gas was set to 100% air, and the DO controller was set to maintain 10% DO by cascading the rpm, not exceeding a maximum rpm of 300 or a minimum of 50 rpm, as in the previous example. After 9 h, the cell densities had increased to $OD_{600}$ of ≈20 (≈3 g cdw/l) when the sparging gas was switched from air to 90% $N_2$, and the maximum rpm was increased to 500.

Figure 4:
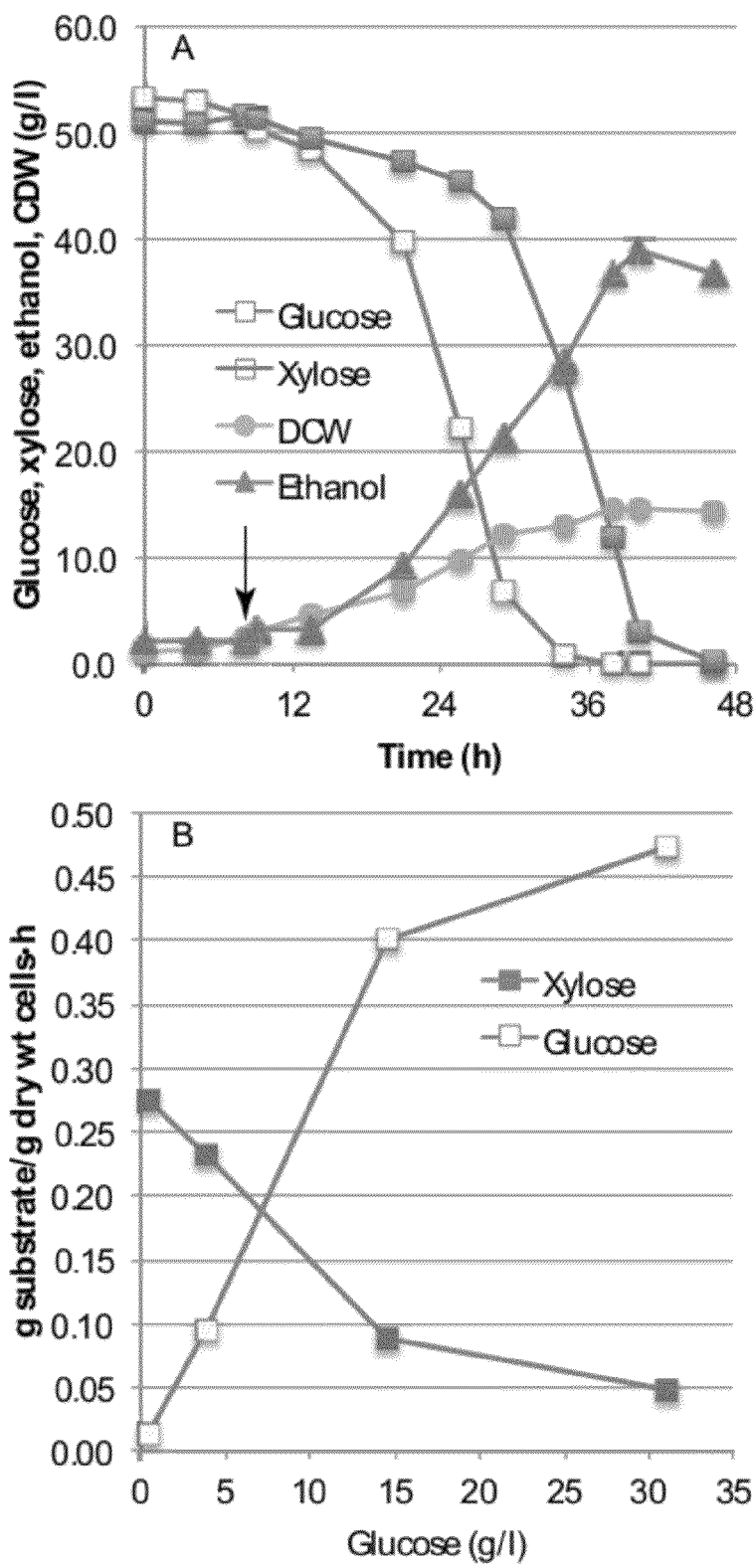
FIG. 4 is a set of graphs showing fermentation of a mixture of glucose and xylose by *Spathaspora passalidarum* NN245 with low initial cascading aeration control at 10% of air saturation followed by sparging with 2.1% oxygen (10% air) at 9 h into the fermentation. Fermentation showing glucose, xylose, cell dry weight (cdw) and ethanol as a function of the fermentation time (A).

When glucose and xylose are present as a 50:50 mixture, glucose is consumed first, but the two sugars are co-utilized (FIG. 4). The initial rate of xylose utilization is relatively low, but it increases steadily as the concentration of glucose falls. At glucose concentrations between 40 and 50 g/l, the specific rate of xylose utilization is less than 0.05 g substrate/g cdw·h. As the concentration of glucose falls from 30 g/l to 15 g/l, the specific xylose utilization rate doubles from 0.05 g/g cdw·h to about 0.1 g/g cdw·h and continues to increase to about 0.3 g/g cdw·h as the glucose concentration falls to zero. While the ethanol yield was less than achieved with cultivation on xylose alone, it was greater than what was observed with glucose alone (FIG. 3). Therefore, cultivation in a glucose/xylose mixture can result in a higher yield of ethanol than from glucose alone.

Based on these results, it can be hypothesized that when the glucose concentration is 30 g/l or less and the concentration of xylose is 40 g/l or more, glucose and xylose will be co-utilized with the concomitant production of ethanol at a yield approaching 0.4 g/g. Other techniques such as cultivation of the inoculum on a medium predominantly containing xylose could increase the relative rate of xylose fermentation in the presence of glucose.

Example 5

Fermentation of Cellobiose

Cells of *Spathaspora passalidarum* NN245 were transferred from a 24-48 h-old plate of YPG into 50 ml of YP medium containing 50 g/l of cellobiose as the sole carbon source. Cultures were incubated at 30° C. with shaking at 200 rpm for 24 h. Fifty ml of whole broth with cells were transferred to 200 ml of the same medium in a 1-liter Erlenmeyer flask and incubation was continued for an additional 24 h. The whole broth (250 ml) was used to inoculate 1750 ml of CBS medium with 50 g/l cellobiose as the sole carbon source. The DO level was set initially to 10% of saturation while sparging with air, as in the previous example. Aeration was regulated by cascading agitation in the range of 50 to 300 rpm. After 12 h of growth when the cell density attained ≈8 g/l, the sparging gas was switched from air to 90% $N_2$ and ethanol production commenced.

Figure 5:
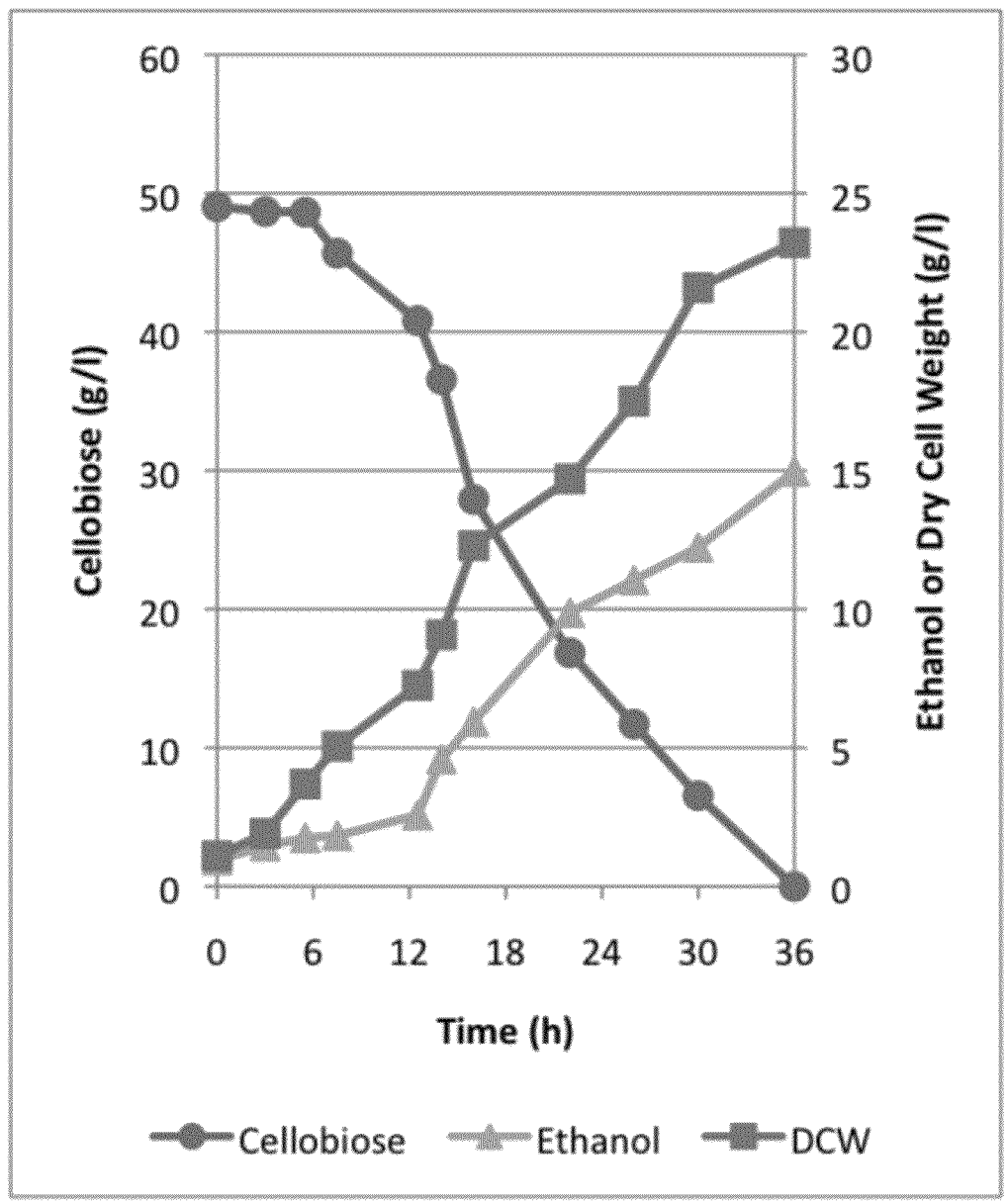
FIG. 5 is a graph showing the fermentation of cellobiose by *Spathaspora passalidarum* NN245 with low initial cascading aeration control at 10% of air saturation followed by sparging with 2.1% oxygen (10% air) beginning at 12 h.

In the subsequent 24 h, the cultures consumed 40 g/l cellobiose while producing ≈11.5 g/l ethanol. This could account for ≈25 g/l of the cellobiose consumed, when the co-production of an equal amount of carbon dioxide is assumed. The remaining cellobiose was converted into cell mass (FIG. 5).

Example 6

Cofermentation of Glucose, Xylose, and Cellobiose

Figure 6:
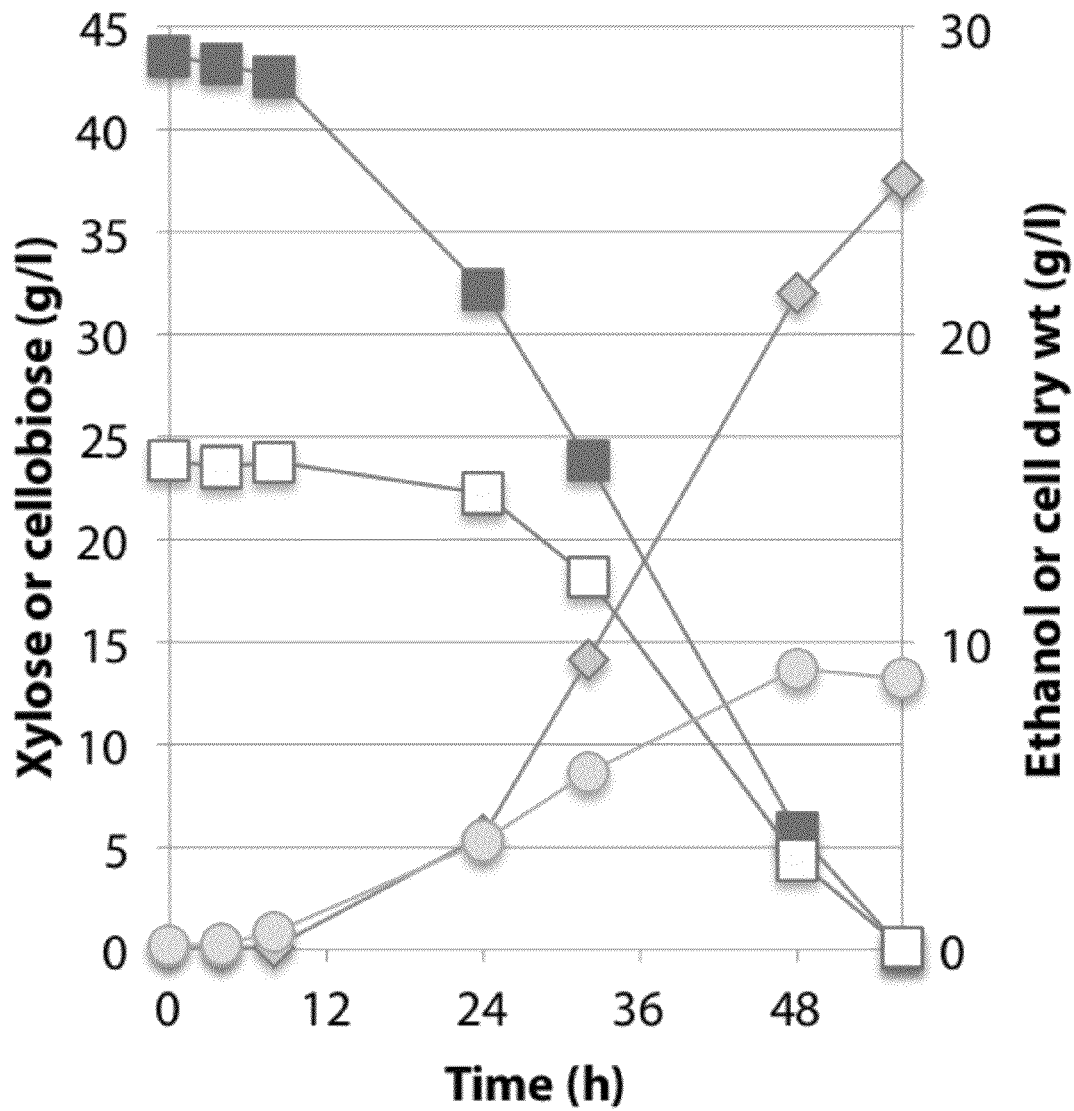
FIG. 6 is a graph showing co-fermentation of cellobiose and xylose under oxygen limitation in triplicate shake flasks. Symbols: xylose, solid squares; cellobiose, open squares; ethanol, diamonds; cell mass, circles. Minimal defined medium (CBS) was employed. Flasks were incubated at 30° C. and shaken at 200 rpm.
Figure 7:
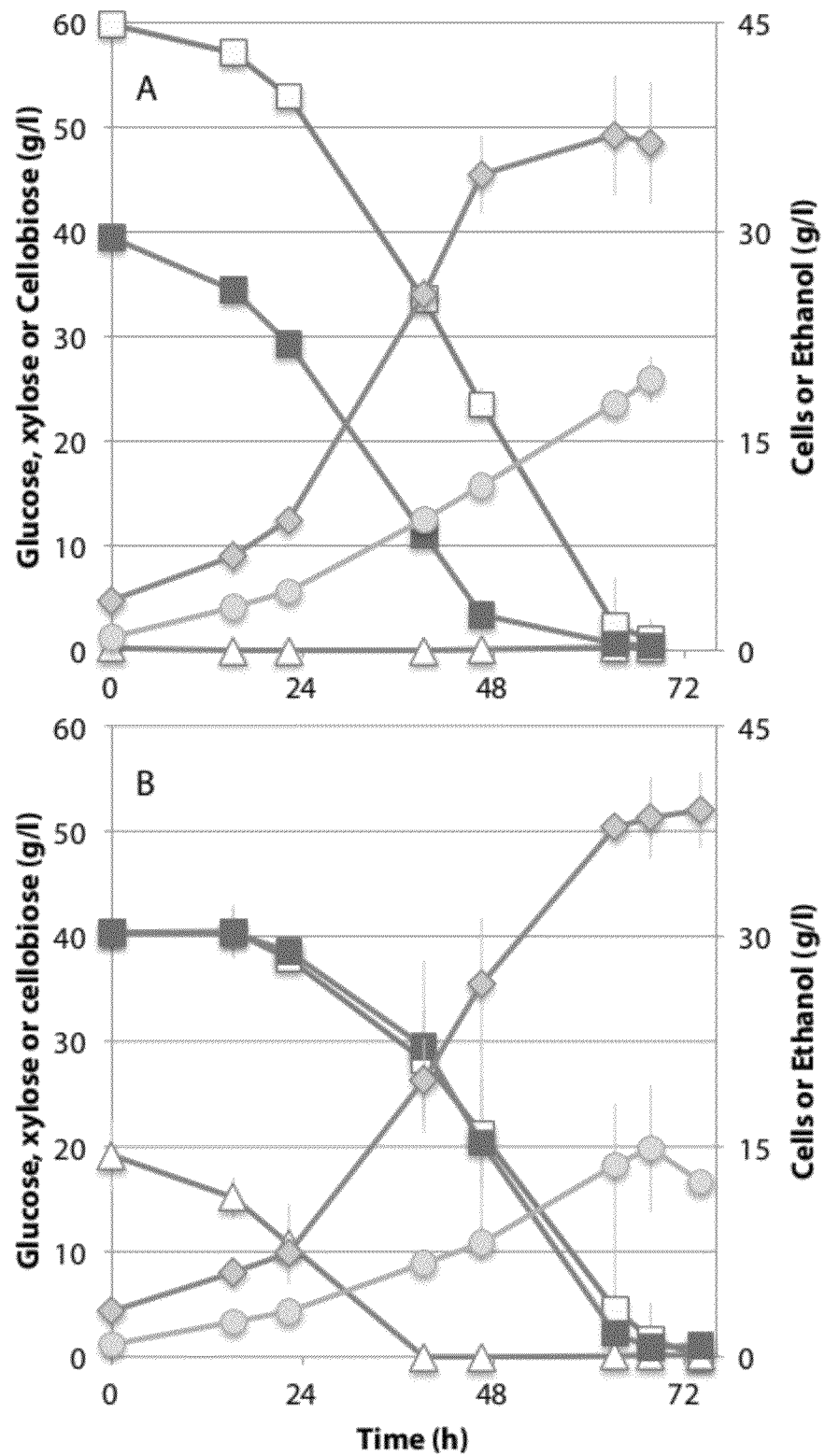
FIG. 7 is a set of graphs showing co-utilization of glucose, xylose, and cellobiose by *Spathaspora passalidarum*. Symbols: glucose, open triangles; xylose, closed squares, cellobiose, open squares, ethanol, diamonds; cell mass, circles.

During enzymatic saccharification and fermentation of pretreated lignocellulosics, the major sugars present are xylose and glucose, xylan oligosaccharides (from hydrolysis of hemicellulose), and cellobiose (from enzymatic saccharification of pretreated cellulosic solids). We therefore examined the simultaneous co-fermentation of cellobiose and xylose. In duplicate shake flasks, the xylose consumption rate was much greater than that for cellobiose, but after cells attained a density of ≧5 g/l, oxygen-limitation induced ethanol production. Cellobiose and xylose were co-utilized at 0.49 and 0.94 g/l·h, respectively, and volumetric ethanol production rate was 0.56 g/l·h (FIG. 6). In bioreactors, cellobiose and xylose were simulataneously co-fermented from the outset at very similar rates in the presence (FIG. 7A) or absence (FIG. 7B) of 20 g/l glucose. Prior to inoculation, $dO_2$ was 2.1%, but this declined to near zero shortly after inoculation. During the fermentation phase, $dO_2$ occasionally rose slowly to ~0.2-0.5% without apparent effect on ethanol production or growth. In the absence of glucose, xylose and cellobiose were simulataneously co-metabolized at essentially similar rates until xylose was depleted at 48 h (FIG. 7A). The rate of ethanol production declined significantly thereafter, but cell growth continued. In the presence of glucose, co-utilization of cellobiose and xylose was delayed slightly in the first 15 h, but all three sugars were co-utilized at very similar rates from 15 to 68 h, at which point all sugars were consumed and ethanol production ceased (FIG. 7B). Maximum ethanol production rate from a mixture of xylose and cellobiose was 1.07 g/l·h, and from all three sugars it was 0.73 g/l·h. Ethanol yields during the phase of maximum production rate were 0.43 g/g and 0.42 g/g for xylose/cellobiose and glucose/xylose cellobiose mixtures, respectively.

Example 7

Fermentation of an AFEX Hydrolysate by Adapted Yeast

In this experiment, the performance of strains of *Spathaspora passalidarum* NN245 that had been adapted to growth and fermentation by cultivation in hydrolysates of loblolly pine and mixed southern hardwoods or corn stover were assessed for the ability to ferment an AFEX hydrolysate of corn, which has been shown to have lower concentrations of toxic compounds and lower acetic concentration (1.5 g/l) compared to hydrolysates obtained by acid treatment.

The starting inocula had been cultured in AFEX hydrolysate for 130 h prior to inoculation. The yeast strains used for inoculum development had been adapted to growth in various hydrolysates for 1 month. Fermentations were carried out in 50 ml of defined minimal medium [modified from Slininger, 2006 (20)] in a /125 ml Erlenmeyer flask, at 30° C., 100 rpm.

The modified Slininger defined minimal medium contained per liter the following nutrients: urea, 2.4 g; $KH_2PO_4$, 1 g, $K_2HPO_4$, 1 g; minimal trace element solution, 1 ml; Slininger's minimal vitamin solution, 2 ml. The minimal trace element solution contained the following per liter: $FeSO4.7H_2O$, 50 g; $ZnSO4.7.H_2O$, 5.5 g; $CuSO_4.5H_2O$, 8 g. Slininger's minimal vitamins solution contains vitamins in the following amounts (mg/l): Biotin, 250; calcium pantothenate, 250; thiamin-HCl, 250; pyridoxine-HCl, 250; nicotinic acid, 250; p-aminobenzoic acid, 250; Vitamin $B_{12}$, 25. The initial cell density had an $OD_{600}$ of 0.5 (≈0.075 mg/ml).

Figure 8:
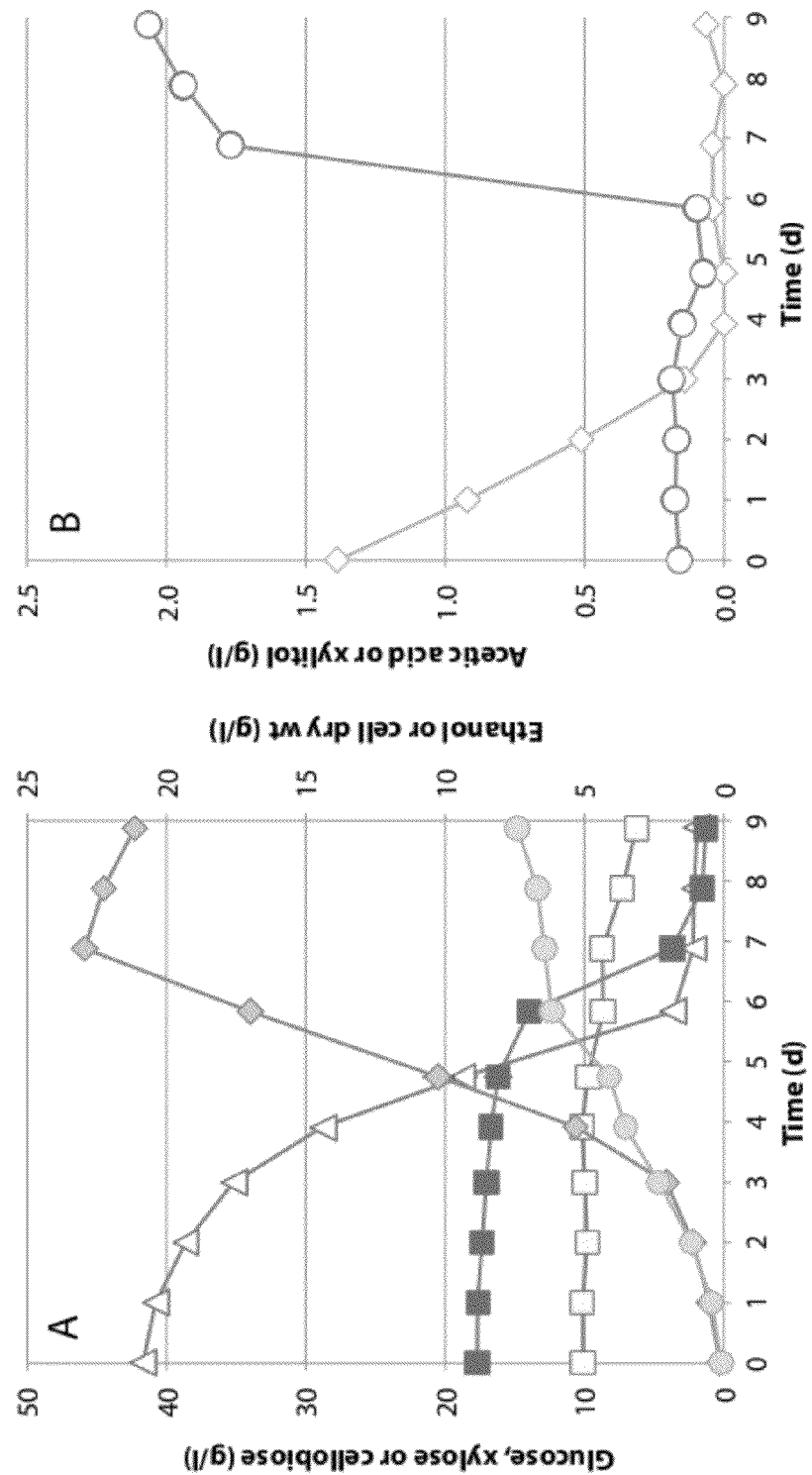
FIG. 8 is a set of graphs showing fermentation of an AFEX hydrolysate by *Spathaspora passalidarum* AF2 in defined minimal medium (Slininger). Fermentation was conducted in duplicate shake flasks (50 ml/125 ml shaken at 100 rpm). AF2 was cultured in a 125-ml Erlenmeyer flask containing 50 ml of AFEX hydrolysate medium at 100 rpm and 30° C. for 5 d (OD above 40) and then transferred directly from adapted flask into another flask containing the same AFEX hydrolysate medium. The initial targeted $OD_{600}$ was 0.5. Duplicate flask fermentations were conducted at 30° C. with rotary shaking at 100 rpm. The starting cell density was 0.1 mg cdw/ml. Symbols: (A) glucose, open triangles; xylose, closed squares, cellobiose, open squares, ethanol, gray diamonds; cell mass, gray circles; (B) acetic acid, open diamonds; xylitol open circles. Averages of two shake flasks are shown.

The AFEX hydrolysate contained ~2.3 times more glucose than xylose. Fermentation time with AFEX was relatively long (FIG. 8A). Its initial acetic acid concentration was about 1.4 g/l. Cells grew under these conditions but did not exhibit significant ethanol production until acetic acid was depleted at 3 d (FIG. 8B). Xylose utilization was largely delayed while glucose was consumed, but after 6 d, strains adapted to growth in hydrolysate rapidly converted 84% of the xylose into 23 g/l ethanol with a yield of 0.45 and 16% into xylitol. Unadapted yeast produced ≈20 to 20.5 g/l ethanol within 6 days, while the adapted NN245_SH2 produced ≈23 g/l ethanol in 7 days. The adapted NN245_SH2 also showed the highest ethanol yield (0.428 g ethanol/g substrate consumed). The adapted yeast consumed the xylose more completely than unadapted yeast and eventually attained approximately a 10% higher concentration of ethanol. None of the yeasts consumed significant amounts of cellobiose under the conditions employed here (FIG. 8). As can be seen from the summary of kinetic constants, the ethanol yield from sugars in AFEX hydrolysate was estimated to be approximately 88% of the maximum theoretical attainable by fermentation (0.51 g/g) (Table 4).

TABLE 4

Performance of adapted cells in AFEX hydrolysate

| Kinetic factor | Time | Volumetric | Specific |
| --- | --- | --- | --- |
| Max ethanol productivity | day 4-7 | 0.248 g/l · h | 0.051 g/g cdw · h |
| Max substrate utilization | day 4-7 | 0.314 g/l · h | 0.064 g/g cdw · h |
| Ethanol yield | Overall | | 0.447 g EtOH/g substrate | cdw = Cell Dry Wt

Example 8

Comparison of Adapted and Un-Adapted *Spathaspora passalidarum* on Maple Hydrolysate The parental strain of the adapted strain NN245_E4 was *S. passalidarum* NN245_SH2, which had has been continually growing and fermenting on wood hydrolysates for more than 1 month. Following this serial subculture, NN245_E2 was suspended in 30% glycerol and frozen at −80° C. In preparation for fermentation, NN245_SH2 was sampled from the −80° C. frozen stock, streaked onto a plate of YPX agar and cultivated for 24 to 48 h at 30° C. Cells from the fresh plate were then cultivated in 4% YPX broth for 16 to 24 h. An adequate amount of cells was then transferred from YPX broth into a 50-ml of corn stover hydrolysate medium, which contained 20 ml of corn stover hydrolysate along with water and other nutrients, to attain an initial $OD_{600}$ of ≈0.5. The corn stover hydrolysate medium had the same composition of nutrients, trace metals, and vitamins as in Example 7. Corn stover hydrolysate medium contained about 80 g/l xylose, 50 g/l glucose and 1.8 g/l of acetic acid.

After the cells were cultivated at 30° C., 100 rpm for about 140 h, a volume (0.5 ml) of culture was transferred into fresh corn stover hydrolysate medium to attain an initial $OD_{600}$ of about 0.1 to 0.5. Transferring a volume (200 µl) of culture into 50 ml of fresh corn stover hydrolysate medium every 72 to 96 hours continued the process of adapting cells to corn stover hydrolysate medium. This inoculum was sufficient to attain an $OD_{600}$≈0.1 at the start of each subculture cycle. *S. passalidarum* NN245_E4 had been sub-cultured in corn stover hydrolysate medium for four passages following the initial recovery of NN245_SH2 from the frozen stock. This corresponded to about 21 days of serial subculture. After 21-days of adaptation in the corn stover hydrolysate, an adequate amount of cell suspension was transferred directly into a 50-ml Erlenmeyer flask containing maple hydrolysate medium to attain an initial $OD_{600}$ of ≈3 to 5. An appropriate volume of un-adapted NN245 suspension from a previously frozen stock culture that had not been exposed to hydrolysate was also directly transferred into a 50-ml maple hydrolysate medium at same time to attain the same initial $OD_{600}$ as that of the adapted NN245_E4 strain.

The un-adapted NN245 was prepared by transferring from a fresh YPX plate into YPX (4%) broth at 30° C., 200 rpm for 24 to 48 h before inoculation. The maple hydrolysate medium was spiked with 40% glucose concentrate solution to attain a ratio of xylose to glucose close to 2. A sterile solution of minimal salts medium (CBS) containing 2.4 g/l of urea was added prior inoculation. Hydrolysate sugars consisted of 32 g/l glucose and 75 g/l xylose for a total sugar concentration was 111 g/l. Fermentations were carried out at 30° C. with rotary agitation at 100 rpm.

Figure 9:
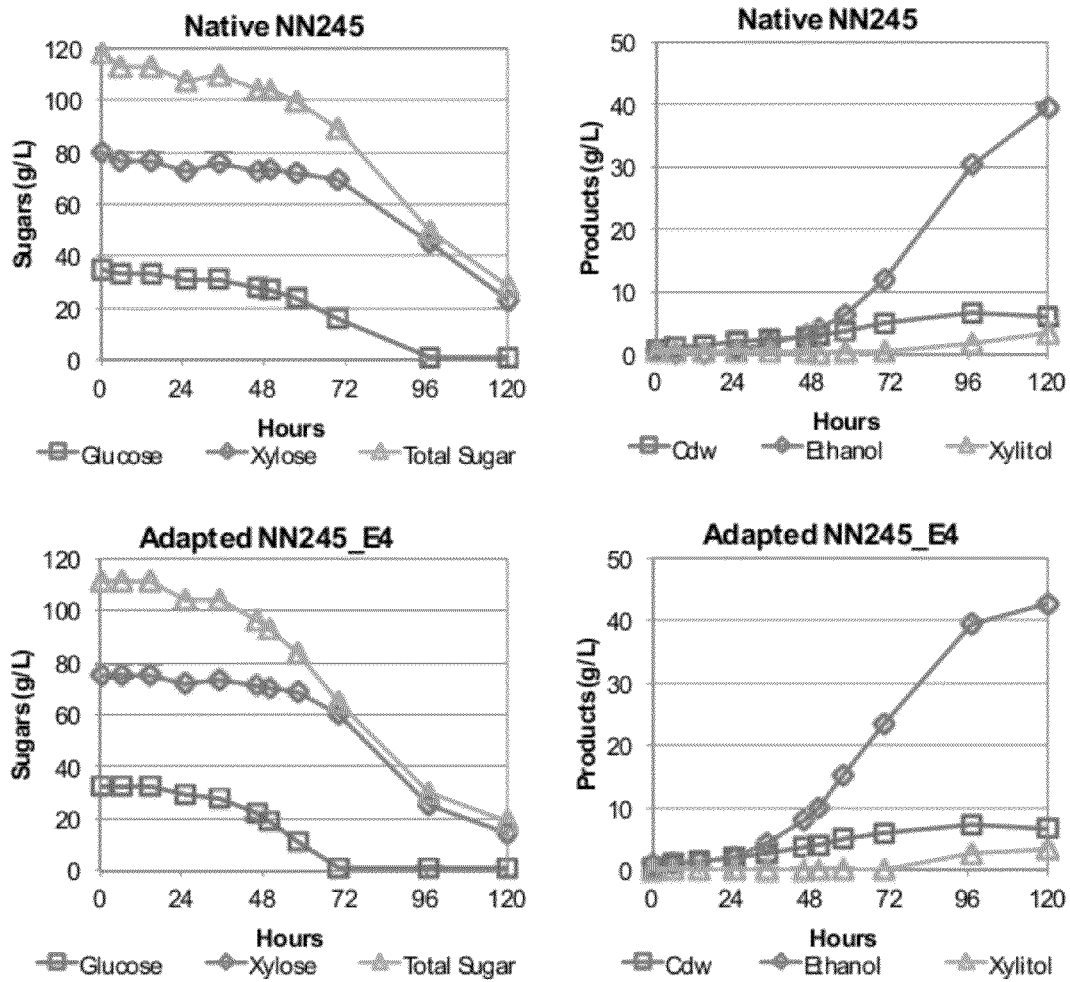
FIG. 9 is a set of graphs showing a comparison of the fermentative abilities of the native *Spathaspora passalidarum* NN245 and a strain of *Spathaspora passalidarum* NN245 that had been adapted by two passages in hydrolysate (NN245_SH2).

The native NN245 strain required 96 h to deplete glucose from the hydrolysate under these conditions. By comparison, the adapted strain depleted all of the glucose within 72 h and depleted a larger fraction of the residual xylose. Co-utilization of glucose and xylose by the adapted NN245_E4 occurred between 46-70 hours with glucose- and xylose-utilization rates of about 0.87 g/l·h and 0.47 g/l·h, respectively. For native NN245, the co-utilization was observed between 72-96 h (FIG. 9). As can be seen from a summation of the fermentation kinetics, the maximal ethanol production rate, the sugar utilization rate and the ethanol yield were 20%, 17% and 3% higher, respectively with the adapted strain than with the un-adapted strain (Table 5).

TABLE 5

Comparison of fermentation kinetics for *Spathaspora passalidarum* un-adapted (NN245) and adapted (NN245_E4) for growth in hydrolysate.

| | NN245 | | NN245_E4 | | |
|---|---|---|---|---|---|
| Strain: | Time span (h) | Rate (g/l · h) | Time span (h) | Rate (g/lh) | Increase (%) |
| Max ethanol production | 58~120 | 0.54 | 46~70 | 0.65 | 20 |
| Max sugar utilization | 58-120 | 1.14 | 46~70 | 1.34 | 17 |
| Max ethanol yield | 58-120 | 0.47 | 46~70 | 0.48 | 3 |

Example 9

Comparison of Adapted *Spathaspora passalidarum* on Maple Hydrolysate and Synthetic Maple Hydrolysate Medium in a 2-Liter Bioreactor The objective of this experiment was to understand and compare the fermentative capacities of a strain of *S. passalidarum* NN245 that had been adapted for growth on hydrolysate when cultivated in a medium containing maple hydrolysate or in a medium containing pure sugars in a ratio similar to that observed in maple hydrolysate. Cells of adapted *S. passalidarum* NN245_E7 that had been adapted in corn stover hydrolysate medium for more than 5 weeks were directly transferred into both 150 ml of maple hydrolysate medium and a mixture of glucose and xylose in 500 ml Erlenmeyer flasks to create starters for 2-l bioreactors.

The maple hydrolysate medium used for inoculation was prepared by following the same method described in example 6. The maple hydrolysate for inoculum preparation contained about 65 g/l of xylose and 35 g/l of glucose and had following nutrients in gram per liter: urea, 2.4 g; MgSO4.7H20, 0.75 g; $KH_2PO_4$, 1 g, $K_2HPO_4$, 1 g; CBS trace element solution, 1 ml; CBS vitamin solution, 1 ml. The pure sugar medium was prepared in a manner to have the same sugar concentration and nutrient level as the maple hydrolysate medium. Cells cultured in maple hydrolysate medium were used as an inoculum for maple hydrolysate bioreactors, and cells cultivated in the pure sugar medium were used to inoculate synthetic maple hydrolysate bioreactors. After 24 h of cultivation at 30° C., 150 rpm, 10 ml of *S. passalidarum* NN245_E8, which was derived from NN245_E7 by cultivation in corn stover hydrolysate for another 5 days, was also added into each flask to increase the cell density. After 58 h of incubation, the $OD_{600}$ of inocula reached 40 to 50 and adequate volumes of cell suspension were transferred into final flasks to have equal cell densities. Sterile water was added to make up the balance of the volume for inoculation and about 120 ml of seed inoculum was added into one bioreactor for a final volume of 1.2-liters. The bioreactor contained the same nutrient levels described in Example 1 and the sugar concentrations were 35.3±1.9 g/l of glucose and 64.6±3.9 g/l of xylose for maple hydrolysate bioreactors and 36±0.3 g/l of glucose and 63.9±0.2 of xylose for synthetic maple hydrolysate bioreactors. DO controllers were calibrated to 10% saturation by sparging with 90% nitrogen and 10% air. The sparging gas was 10% air in the beginning and agitators was set to maintain 10% DO by cascading the rpm with a minimum of 400 rpm and a maximum of 500 rpm during whole fermentation process. The sparging rate was maintained at 0.25 vvm, which was corresponded to 0.3 l/min in a 1.2 l final liquid volume in a bioreactor. For Example 9, the bioreactor temperature was controlled at 30° C. and pH was kept constant at 5.0±0.1 by automatic addition of 5 N KOH. After 11 h, the sparging gas was switched from air to 10% air (0.21% oxygen).

Figure 10:
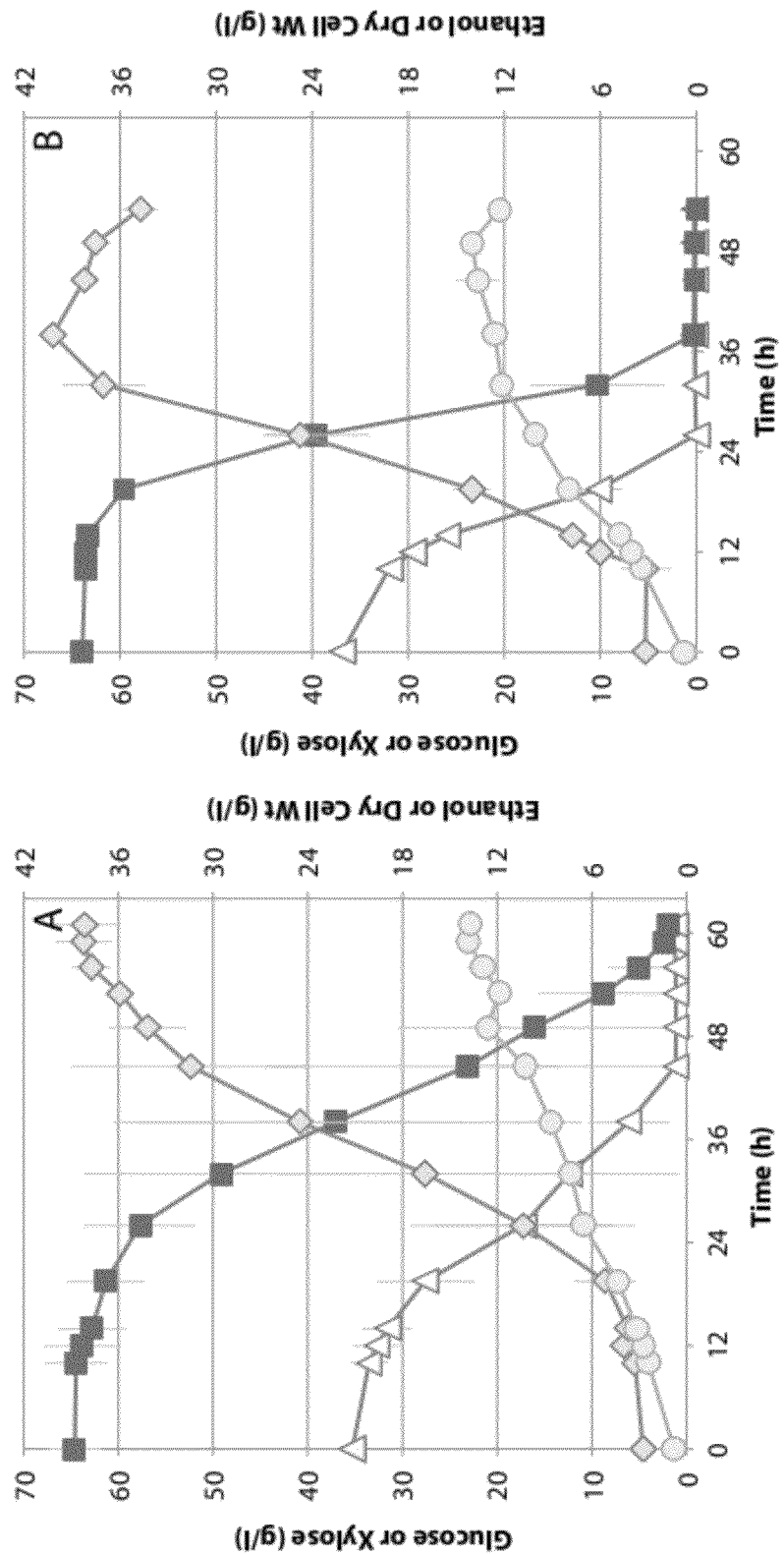
FIG. 10 is a set of graphs showing fermentation of a maple hemicellulose hydrolysate (MHH) (A) and a synthetic sugar mixture (B) by *Spathaspora passalidarum* E7 in defined minimal medium (CBS). Solid symbols, xylose; open symbols, glucose; squares, sugar; circles, cell mass; diamonds, ethanol. Averages of two bioreactors is shown with range of values (grey bars).

In the mixture of pure sugars, fermentation of glucose and xylose were essentially complete within 36 h. Ethanol production commenced immediately following the switch to 2.1% oxygen, and was complete within 36 h. Glucose and xylose were consumed concomitantly once oxygen limitation was initiated. All of the glucose was consumed within ≈24 h and all of the xylose was consumed within ≈36 h. The average ethanol yield from the mixed sugars was ≈0.48 between 11 and 35 h of cultivation (FIG. 10A).

In the fermentation of maple hydrolysate, ethanol production commenced shortly after the sparging gas was switched to 2.1% air and was complete within 60 h. Glucose and xylose were consumed concomitantly once oxygen limitation was initiated. Consumption of glucose was complete within 48 h and consumption of xylose was complete within 60 h. The average yield of ethanol from the mixed sugars was ≈0.40 between 23 and 57 h of cultivation (FIG. 10B).

Example 10

Comparison of Rich Medium Versus Minimal Medium for Inoculum Preparation

Industrial fermentations for renewable fuels require the use of very low cost nutrients in medium formulations. The fermentations described here had all been carried out with cells in minimal medium (CBS), but inocula preparations had been carried out with rich YP media. The purpose of this experiment was to compare the fermentation kinetics when inocula were cultivated either in minimal (CBS) or rich YP medium.

*Spathaspora passalidarum* NN245 was inoculated into two 125 ml Erlenmeyer flasks containing 50 ml of minimal medium (CBS) with 40 g/l glucose and 40 g/l xylose as carbon sources. These were incubated at 200 rpm, 30° C. for 24 h. These 50 ml glucose/xylose CBS medium cultures were then added to 200 ml of the same medium in a 1-liter Erlenmeyer and incubation was continued with 200 rpm for an additional 24 h. *S. passalidarum* NN245 was also inoculated into two 125 ml Erlenmeyer flasks containing 50 ml of YP(X/G) medium with 40 g/l glucose and 40 g/l xylose as carbon sources. These were incubated at 200 rpm, 30° C. for 24 h. These 50 ml glucose/xylose minimal medium cultures were then added to 200 ml of the same medium in a 1-liter Erlenmeyer and incubation was continued with 200 rpm for an additional 24 h.

All four bioreactors received minimal CBS medium containing glucose and xylose in an appropriate volume of liquid (1750 ml) to give a starting concentration of ≈50 g/l of each sugar after addition of the inoculum. Following autoclaving, the bioreactors were sparged sequentially with air and $N_2$ in order to set the dynamic range for the DO controller. The reactors were then sparged with a mixture of 10% air and 90% $N_2$ in order to set the DO level for 10% of air saturation. The sparging gas was then switched to air, the DO controller was set to maintain 10% of air saturation using a cascade DO control mode with the rpm in a range of 150 to 300 rpm.

The cell densities of the cultures were assayed and an appropriate volume of each culture was used to inoculate each of the bioreactors. Culture volumes were adjusted such that the maximal volume (250 ml) was used with the culture having the lowest cell density. For the other cultures where the cell densities were higher, a smaller volume of culture was used that would deliver the same amount of cells to each bioreactor. The balance of the inoculum culture was then centrifuged aseptically to remove excess cells, and the cell-free, spent broth was used to make up the difference in volume so that the starting volume of each bioreactor was 2000 ml. Due to differences in the characteristics of cells grown under these two conditions, the cell dry wt was about 20% higher in the cells cultivated on minimal medium.

Immediately following inoculation, the DO level began to drop, as previously observed. The DO controller gradually increased rpm as the DO level fell below 10% of saturation. Samples were withdrawn at the time of inoculation and periodically thereafter in order to track cell densities and sugar utilization.

Figure 11:
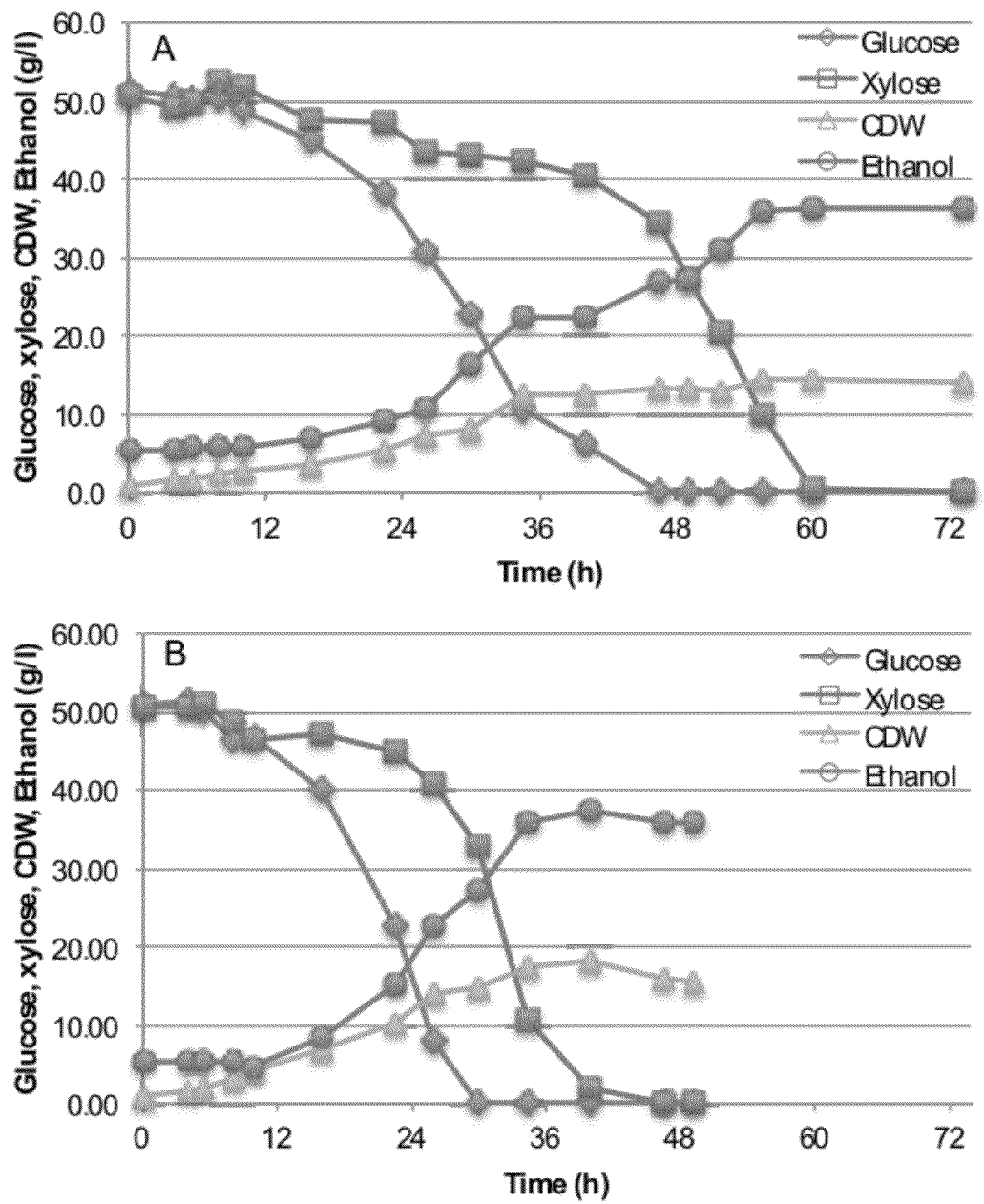
FIG. 11 is a set of graphs showing a comparison of sugar utilization and ethanol production rates by *S. passalidarum* in minimal defined medium with a mixture of glucose and xylose as the carbon source when the inoculum is cultivated either in YP X/G rich medium (A) or in CBS X/G minimal defined medium (B).

After 8 h, cells for which the inoculum had been cultivated in rich medium attained a density of 2.36 g/l; cells for which the inoculum had been cultivated in minimal medium had attained an average density of 3.1 g/l. At this point, the sparging gas was switched from 100% air to 10% air, 90% $N_2$. Ethanol began to accumulate immediately after the transition of 10% air in the case of cell inoculum cultivated in minimal medium, but the accumulation of ethanol was much slower in the case of cells cultivated in rich medium. Co-utilization of glucose and xylose occurred in bioreactors containing inocula from either medium, but it was more gradual and conspicuous in bioreactors containing cells inoculated from rich medium (FIG. 11).

In the case of inocula prepared with rich medium, the volumetric xylose utilization rate remained at or below 0.5 g/l·h until the glucose concentration fell below about 5 g/l. The xylose utilization rate then increased dramatically for a short period of time to a maximal value of 2.5-2.7 g/l·h until xylose was exhausted. In the case of inocula prepared with minimal medium, once the glucose concentration fell below 37 g/l, the xylose utilization rate increased dramatically from about 0.3 to 0.6 g/l·h and reached a maximum rate of 2.8 to 2.9 g/l·h before xylose was exhausted.

This example shows that rapid co-utilization of xylose in the presence of glucose is initiated at a higher concentration of glucose when cells of *S. passalidarum* are propagated in minimal medium than in a rich medium prior to fermentation. It also shows that co-utilization of xylose and glucose occurs when cells are propagated in a rich medium.

REFERENCES

1. Akhtar M, Kenealy W R, Horn E, & Ross E S (2009) US 2009/0194243 A1.
2. Lee J W, Rodrigues R C L B, & Jeffries T W (2009) Simultaneous saccharification and ethanol fermentation of oxalic acid pretreated corncob assessed with response surface methodology. (Translated from English) *Bioresource Technology* 100(24):6307-6311 (in English).
3. Lee J W, Rodrigues R C L B, Kim H J, Choi I G, & Jeffries T W (2010) The roles of xylan and lignin in oxalic acid pretreated corncob during separate enzymatic hydrolysis and ethanol fermentation. (Translated from English) *Bioresource Technology* 101(12):4379-4385 (in English).
4. Scordia D, Cosentino S L, & Jeffries T W (2010) Second generation bioethanol production from *Saccharum spontaneum* L. ssp *aegyptiacum* (Willd.) Hack. (Translated from English) *Bioresource Technology* 101(14):5358-5365 (in English).
5. Izumi Y, Sugiura J, Hitoshi K, & Naoya A (2005) 6942754 B2.
6. Kurtzman C P & Suzuki M (2010) Phylogenetic analysis of ascomycete yeasts that form coenzyme Q-9 and the proposal of the new genera *Babjeviella, Meyerozyma, Millerozyma, Priceomyces*, and *Scheffersomyces*. *Mycoscience* 51(1):2-14.
7. Jeffries T W & Kurtzman C P (1994) Strain selection, taxonomy and genetics of xylose fermenting yeasts. *Enzyme and Microbial Technology* 16(11):922-932.
8. Vanderwalt J P, Ferreira N P, & Steyn R (1987) *Candida lyxosophila* sp. nov., a new D-xylose fermenting yeast from Southern Africa. *Antonie Van Leeuwenhoek Journal of Microbiology* 53(2):93-97.
9. Nguyen N H, Suh S O, Marshall C J, & Blackwell M (2006) Morphological and ecological similarities: wood-boring beetles associated with novel xylose-fermenting yeasts, gen. sp nov and *Candida jeffriesii* sp nov. *Mycological Research* 110:1232-1241.
10. Cadete R M, et al. (2009) *Spathaspora arborariae* sp nov., a D-xylose-fermenting yeast species isolated from rotting wood in Brazil. *Fems Yeast Research* 9(8):1338-1342.
11. Alves L A, Felipe M G A, Silva J, Silva S S, & Prata A M R (1998) Pretreatment of sugarcane bagasse hemicellulose hydrolysate for xylitol production by *Candida guilliermondii*. (Translated from English) *Applied Biochemistry and Biotechnology* 70-2:89-98 (in English).
12. Lin Y P, et al. (2010) The Alcohol Dehydrogenase System in the Xylose-Fermenting Yeast *Candida maltosa*. *Plos One* 5(7).
13. Vongsuvanlert V & Tani Y (1989) Xylitol production by a methanol yeast, *Candida boidinii* (Kloeckers sp.) NO-2201. (Translated from English) *Journal of Fermentation and Bioengineering* 67(1):35-39 (in English).
14. Jeffries T W, et al. (1994) Genetic engineering of the xylose-fermenting yeast *Pichia stipitis* for improved ethanol production. *Abstracts of Papers of the American Chemical Society* 207:167-BTEC.
15. Yang V W, Marks J A, Davis B P, & Jeffries T W (1994) High efficiency transformation of *Pichia stipitis* based on its URA3 gene and a homologous authomous replication sequence, ARS2. *Applied and Environmental Microbiology* 60(12):4245-4254.

16. Jeffries T W, et al. (2007) Genome sequence of the lignocellulose-bioconverting and xylose-fermenting yeast *Pichia stipitis*. *Nature Biotechnology* 25(3):319-326.
17. Jeffries T W & Van Vleet J R H (2009) *Pichia stipitis* genomics, transcriptomics, and gene clusters. *Fems Yeast Research* 9(6):793-807.
18. Barbosa A C, Cadete R M, Gomes F C O, Lachance M A, & Rosa C A (2009) *Candida materiae* sp nov., a yeast species isolated from rotting wood in the Atlantic Rain Forest. *International Journal of Systematic and Evolutionary Microbiology* 59:2104-2106.
19. Jeffries T W (1983) Effects of nitrate on fermentation of xylose and glucose by *Pachysolen tannophilus*. *Bio/Technology* 1(6):503-506.
20. Slininger P J, Dien B S, Gorsich S W, & Liu Z L (2006) Nitrogen source and mineral optimization enhance D-xylose conversion to ethanol by the yeast *Pichia stipitis* NRRL Y-7124. *Applied Microbiology and Biotechnology* 72(6):1285-1296.
21. Dupreez J C, Vandriessel B, & Prior B A (1989) Effect of aerobiosis on fermentation and key enzyme levels during growth of *Pichia stipitis*, *Candida shehatae* and *Candida tenuis* on D-xylose. *Archives of Microbiology* 152(2):143-147.
22. Dupreez J C, Vandriessel B, & Prior B A (1989) Fermentation of D-xylose by *Candida shehatae* and *Pichia stipitis* at low dissolved oxygen levels. *Yeast* 5:129-130.
23. Ligthelm M E, Prior B A, & Dupreez J C (1988) The oxygen requirements of yeasts for the fermentation of D-xylose and D-glucose to ethanol. *Applied Microbiology and Biotechnology* 28(1):63-68.
24. Slininger P J, Bothast R J, Ladisch M R, & Okos M R (1990) Optimum pH and temperature conditions for xylose fermentation by *Pichia stipitis*. *Biotechnology and Bioengineering* 35(7):727-731.
25. Belinchon M M & Gancedo J M (2007) Glucose controls multiple processes in *Saccharomyces cerevisiae* through diverse combinations of signaling pathways. *Fems Yeast Research* 7(6):808-818.
26. Gancedo J M (1998) Yeast carbon catabolite repression. (Translated from English) *Microbiology and Molecular Biology Reviews* 62(2):334-+(in English).
27. Kim J H, Block D E, & Mills D A (2010) Simultaneous consumption of pentose and hexose sugars: an optimal microbial phenotype for efficient fermentation of lignocellulosic biomass. *Applied Microbiology and Biotechnology* 88(5):1077-1085.
28. Lee H (1992) Reversible inactivation of D-xylose utilization by D-glucose in the pentose fermenting yeast *Pachysolen tannophilus*. (Translated from English) *Fems Microbiology Letters* 92(1):1-4 (in English).
29. Jeffries T W, Fady J H, & Lightfoot E N (1985) Effect of glucose supplements on the fermentation of xylose by *Pachysolen tannophilus*. *Biotechnology and Bioengineering* 27(2):171-176.
30. Sreenath H K & Jeffries T W (1999) 2-deoxyglucose as a selective agent for derepressed mutants of *Pichia stipitis*. *Applied Biochemistry and Biotechnology* 77-9:211-222.
31. Young E, Lee S M, & Alper H (2010) Optimizing pentose utilization in yeast: the need for novel tools and approaches. (Translated from English) *Biotechnology for Biofuels* 3 (in English).
32. Runquist D, Hahn-Hagerdal B, & Radstrom P (2010) Comparison of heterologous xylose transporters in recombinant *Saccharomyces cerevisiae*. *Biotechnology for Biofuels* 3.
33. Gururajan V T, Gorwa-Grauslund M F, Hahn-Hagerdal B, Pretorius I S, & Otero R R C (2007) A constitutive catabolite repression mutant of a recombinant *Saccharomyces cerevisiae* strain improves xylose consumption during fermentation. *Annals of Microbiology* 57(1):85-92.
34. Gururajan V T, Van Rensburgi P, Hahn-Hagerdal B, Pretorius I S, & Otero R R C (2007) Development and characterisation of a recombinant *Saccharomyces cerevisiae* mutant strain with enhanced xylose fermentation properties. *Annals of Microbiology* 57(4):599-607.
35. Yarrow D (1998) Methods for the isolation, maintenance and identification of yeasts. *The Yeasts, a Taxonomic Study*, (Elsevier, Amsterdam), 4th Ed, pp 77-100.
36. Barnett J A, Payne R W, & Yarrow D (2000) *Yeasts* (Cambridge University Press, Cambridge) 3rd Ed.
37. Verduyn C, Postma E, Scheffers W A, & Vandijken J P (1992) Effect of benzoic acid on metabolic fluxes in yeasts—a continuous culture study on the regulation of respiration and alcoholic fermentation. *Yeast* 8(7):501-517.

What is claimed is:

1. A method of producing ethanol comprising contacting a mixture comprising xylose and glucose with a *Spathaspora passalidarum* yeast under conditions suitable to allow the yeast to ferment at least a portion of the xylose to ethanol either before or during the same time the yeast is fermenting the glucose; wherein the yeast is *Spathaspora passalidarum* NN245, deposited with the Agricultural Research Service as Deposit Number NRRL Y-50740.

2. The method of claim 1, wherein the yeast is *Spathaspora passalidarum* adapted for growth in a hydrolysate.

3. The method of claim 1, wherein the glucose is less than or equal to about 30 g/l of the mixture.

4. The method of claim 1, wherein the conditions are suitable for fermentation of at least a portion of the glucose to ethanol.

5. The method of claim 1, wherein the mixture further comprises cellobiose.

6. The method of claim 5, wherein the conditions are suitable for fermentation of at least a portion of the cellobiose to ethanol.

7. The method of claim 6, wherein the conditions include oxygen limitation.

8. The method of claim 7, wherein the oxygen is less than or equal to about 2.1% in the mixture.

9. The method of claim 1, wherein the mixture further comprises cellobiose.

10. The method of claim 9, wherein the conditions are suitable for fermentation of at least a portion of the glucose and a portion of the cellobiose to ethanol.

11. The method of claim 10, wherein the conditions include oxygen limitation.

12. The method of claim 10, wherein the oxygen is less than or equal to about 2.1% in the mixture.

13. The method of claim 1, wherein the mixture is a hydrolysate.

14. The method of claim 13, wherein the hydrolysate is from corn stover, grain hulls, corn cobs, sugarcane bagasse, wood chips, wood pulp, softwood, hardwood, pine, loblolly pine, maple, switchgrass (*Pancium virgatum*), *Miscanthus*, date palm (*Phoenix dectylifera*), oil palm, *Sorghum*, or *Arundo donax*.

15. The method of claim 13, wherein the hydrolysate is an enzymatic or acid hydrolysate.

16. The method of claim 13, wherein the hydrolysate is an acid hydrolysate, and wherein the yeast is adapted to growth in acidic conditions prior to contact with the mixture.

17. The method of claim 16, wherein the yeast is adapted to growth in at least 3.0 acetic acid.

18. The method of claim 13, wherein the hydrolysate is subjected to saccharification either before or simultaneous with the method.

19. The method of claim 1, wherein the rate of ethanol production is greater than or equal to about 0.5 g/lh.

20. The method of claim 1, wherein the amount of ethanol produced per gram of sugar in the mixture is greater than or equal to about 0.3 grams per gram sugar.

* * * * *